(12) United States Patent
Vito et al.

(10) Patent No.: US 8,142,382 B2
(45) Date of Patent: Mar. 27, 2012

(54) VIBRATION DAMPENING MATERIAL AND METHOD OF MAKING SAME

(75) Inventors: Robert A. Vito, Berwyn, PA (US); Carmen N. DiMario, West Chester, PA (US); Thomas Falone, Mickleton, NJ (US)

(73) Assignee: Matscitechno Licensing Company, Kennett Square, PA (US)

( * ) Notice: Subject to any disclaimer, the term of this patent is extended or adjusted under 35 U.S.C. 154(b) by 1637 days.

(21) Appl. No.: 10/958,745

(22) Filed: Oct. 5, 2004

(65) Prior Publication Data
US 2005/0137514 A1    Jun. 23, 2005

Related U.S. Application Data

(60) Continuation-in-part of application No. 10/856,215, filed on May 28, 2004, now Pat. No. 6,942,586, which is a continuation of application No. 10/659,560, filed on Sep. 10, 2003, now Pat. No. 6,935,973, which is a division of application No. 09/939,319, filed on Aug. 27, 2001, now Pat. No. 6,652,398.

(51) Int. Cl.
| | |
|---|---|
| *B32B 21/02* | (2006.01) |
| *B32B 21/10* | (2006.01) |
| *B32B 17/12* | (2006.01) |
| *B32B 18/00* | (2006.01) |
| *B32B 5/08* | (2006.01) |
| *C08L 15/00* | (2006.01) |
| *A61F 13/06* | (2006.01) |
| *A61L 15/00* | (2006.01) |
| *D04B 1/14* | (2006.01) |
| *D04B 21/14* | (2006.01) |
| *D04B 1/18* | (2006.01) |
| *D04B 7/16* | (2006.01) |
| *D04B 11/12* | (2006.01) |
| *D04B 7/00* | (2006.01) |

(52) U.S. Cl. ................ 602/75; 602/60; 602/61; 602/62; 442/269; 442/305; 442/306; 442/307; 442/308; 428/293.1; 428/293.4; 428/295.4; 523/111

(58) Field of Classification Search .............. 602/60–66, 602/75, 903; 442/269, 305–308; 428/293.1, 428/293.4, 295.4; 523/111
See application file for complete search history.

(56) References Cited

U.S. PATENT DOCUMENTS 1,125,029  A    1/1915   Lard
(Continued)

FOREIGN PATENT DOCUMENTS

DE        2805314        8/1979
(Continued)

OTHER PUBLICATIONS

Database WIP Week 198711, Derwent Publications Ltd., London, GB; AN 1987-075332, Feb. 5, 1987 (Abstract).

*Primary Examiner* — Patricia Bianco
*Assistant Examiner* — Brandon Jackson
(74) *Attorney, Agent, or Firm* — RatnerPrestia

(57) ABSTRACT

A material having a stretch axis and adapted to regulate energy by distributing and partially dissipating energy exerted thereon. The material includes a material body elongateable along the stretch axis from a first position to a second position, in which the material body is elongated by a predetermined amount relative to the first position. The material body includes a first elastomer layer defining a material length and a planar support structure disposed within the elastomer layer generally along the stretch axis in an at least partially non linear fashion while the material body is in the first position so that a length of the support structure, as measured along a surface thereof, is greater than the material length of the first elastomer layer.

54 Claims, 18 Drawing Sheets

U.S. PATENT DOCUMENTS

| | | |
|---|---|---|
| 1,195,994 A | 8/1916 | Lard |
| 1,498,838 A | 6/1924 | Harrison, Jr. |
| 1,551,203 A | 8/1925 | Mills |
| 1,620,118 A | 3/1927 | Mattern |
| 1,701,856 A | 2/1929 | Kraeuter |
| 1,772,414 A | 8/1930 | Brooke-Hunt et al. |
| 2,023,131 A | 12/1935 | Gibson |
| 2,099,521 A | 11/1937 | Herkimer et al. |
| 2,871,899 A | 2/1959 | Coyle et al. |
| 3,256,130 A * | 6/1966 | Nisbet et al. ............... 442/314 |
| 3,353,981 A | 11/1967 | Jacob |
| 3,606,326 A | 9/1971 | Sparks et al. |
| 3,716,433 A | 2/1973 | Plummer |
| 3,730,509 A | 5/1973 | Jorn |
| 3,779,551 A | 12/1973 | Wilson |
| 3,791,050 A | 2/1974 | Egtvedt |
| 3,862,882 A | 1/1975 | Marzocchi |
| 4,015,851 A | 4/1977 | Pennell |
| 4,044,625 A | 8/1977 | D'Haem et al. |
| 4,134,198 A | 1/1979 | Briggs |
| 4,143,109 A | 3/1979 | Stockum |
| 4,147,443 A | 4/1979 | Skobel |
| 4,197,611 A | 4/1980 | Bell et al. |
| 4,237,177 A | 12/1980 | Slama et al. |
| 4,261,567 A | 4/1981 | Uffindell |
| 4,268,574 A | 5/1981 | Peccenini et al. |
| 4,338,270 A | 7/1982 | Uffindell |
| 4,347,280 A | 8/1982 | Lau et al. |
| 4,417,042 A | 11/1983 | Dziark |
| 4,483,972 A | 11/1984 | Mitchell |
| 4,526,828 A | 7/1985 | Fogt et al. |
| 4,552,713 A | 11/1985 | Cavicchioli |
| 4,575,446 A | 3/1986 | Schaefer |
| 4,591,160 A | 5/1986 | Piragino |
| 4,597,578 A | 7/1986 | Lancaster |
| 4,613,537 A | 9/1986 | Krupper |
| 4,660,832 A | 4/1987 | Shomo |
| 4,668,563 A * | 5/1987 | Buese et al. ............... 442/314 |
| 4,706,788 A | 11/1987 | Inman et al. |
| 4,736,949 A | 4/1988 | Muroi |
| 4,819,939 A | 4/1989 | Kobayashi |
| 4,864,738 A | 9/1989 | Horovitz |
| 4,912,836 A | 4/1990 | Avetoom |
| 4,919,420 A | 4/1990 | Sato |
| 4,948,131 A | 8/1990 | Nakanishi |
| 4,953,862 A | 9/1990 | Uke et al. |
| 4,983,242 A | 1/1991 | Reed |
| 4,989,643 A | 2/1991 | Walton et al. |
| 5,005,254 A | 4/1991 | Uffindell |
| 5,042,804 A | 8/1991 | Uke et al. |
| 5,083,780 A | 1/1992 | Walton et al. |
| 5,088,734 A | 2/1992 | Glava |
| 5,110,653 A | 5/1992 | Landi |
| 5,122,405 A | 6/1992 | Landi |
| 5,137,769 A | 8/1992 | Landi |
| 5,193,246 A | 3/1993 | Huang |
| 5,199,706 A | 4/1993 | Chen |
| 5,203,561 A | 4/1993 | Lanctot |
| 5,240,247 A | 8/1993 | Didier |
| 5,254,391 A | 10/1993 | Davis |
| 5,258,088 A | 11/1993 | Wu |
| 5,261,665 A | 11/1993 | Downey |
| 5,267,487 A | 12/1993 | Falco et al. |
| 5,269,516 A | 12/1993 | Janes |
| 5,282,618 A | 2/1994 | Hong |
| 5,290,036 A | 3/1994 | Fenton et al. |
| 5,294,119 A | 3/1994 | Vincent et al. |
| 5,319,867 A | 6/1994 | Weber |
| 5,322,280 A | 6/1994 | Wu |
| 5,322,285 A | 6/1994 | Turner |
| 5,322,290 A | 6/1994 | Minami |
| 5,333,861 A | 8/1994 | Mills |
| 5,338,600 A | 8/1994 | Fitchmun et al. |
| 5,339,793 A | 8/1994 | Findley |
| 5,348,303 A | 9/1994 | Swissheim |
| 5,355,552 A | 10/1994 | Huang |
| 5,362,046 A | 11/1994 | Sims |
| 5,377,979 A | 1/1995 | Long |
| 5,384,083 A | 1/1995 | Dawn et al. |
| 5,395,108 A | 3/1995 | Souders et al. |
| 5,435,549 A | 7/1995 | Chen |
| 5,463,824 A | 11/1995 | Barna |
| 5,511,777 A | 4/1996 | McNeely |
| 5,516,101 A | 5/1996 | Peng |
| 5,524,885 A | 6/1996 | Heo |
| 5,528,842 A | 6/1996 | Ricci et al. |
| 5,540,982 A * | 7/1996 | Scholz et al. ............... 442/59 |
| 5,547,189 A | 8/1996 | Billings |
| 5,575,473 A | 11/1996 | Turner |
| 5,593,158 A | 1/1997 | Filice et al. |
| 5,621,914 A | 4/1997 | Ramone et al. |
| 5,624,114 A | 4/1997 | Kelsey |
| D379,208 S | 5/1997 | Kulisek, Jr. |
| 5,636,377 A | 6/1997 | Wiener |
| 5,653,643 A | 8/1997 | Falone et al. |
| 5,655,975 A | 8/1997 | Nashif |
| 5,657,985 A | 8/1997 | Dahlstrom et al. |
| 5,673,437 A | 10/1997 | Chase et al. |
| 5,686,158 A | 11/1997 | Gibbon |
| 5,695,408 A | 12/1997 | DeLaCruz |
| 5,725,487 A * | 3/1998 | Freeman et al. ............... 602/8 |
| 5,730,662 A | 3/1998 | Rens |
| 5,749,798 A | 5/1998 | Kuebler et al. |
| 5,759,113 A | 6/1998 | Lai et al. |
| 5,772,524 A | 6/1998 | Huang |
| 5,789,327 A | 8/1998 | Rousseau |
| 5,840,397 A | 11/1998 | Landi et al. |
| 5,842,933 A | 12/1998 | Lewis |
| 5,843,851 A | 12/1998 | Cochran |
| 5,858,521 A | 1/1999 | Okuda et al. |
| 5,912,195 A | 6/1999 | Walla et al. |
| 5,916,664 A | 6/1999 | Rudy |
| 5,926,847 A | 7/1999 | Eibert |
| 5,944,617 A | 8/1999 | Falone et al. |
| 5,946,734 A | 9/1999 | Vogan |
| 5,963,989 A | 10/1999 | Robertson |
| 5,979,081 A | 11/1999 | Vaz |
| 6,000,062 A | 12/1999 | Trakh |
| 6,007,439 A | 12/1999 | MacKay, Jr. |
| 6,030,355 A | 2/2000 | Callinan et al. |
| 6,074,965 A * | 6/2000 | Bodenschatz et al. ........ 442/269 |
| 6,077,793 A | 6/2000 | Hatjasalo et al. |
| 6,167,639 B1 | 1/2001 | Ventura |
| 6,216,276 B1 | 4/2001 | Eibert |
| 6,219,940 B1 | 4/2001 | Kita |
| 6,231,946 B1 | 5/2001 | Brown, Jr. et al. |
| 6,368,989 B1 | 4/2002 | Pascual et al. |
| 6,416,432 B1 | 7/2002 | Rosen et al. |
| 6,511,927 B1 * | 1/2003 | Ellis et al. ............... 442/77 |
| 6,544,910 B2 * | 4/2003 | Himmelsbach et al. ...... 442/150 |
| 6,558,270 B2 | 5/2003 | Kwitek |
| 6,578,836 B2 | 6/2003 | Kogure et al. |
| 6,969,548 B1 | 11/2005 | Goldfine |
| 7,207,962 B2 * | 4/2007 | Anand et al. ............... 602/8 |
| 7,285,505 B2 * | 10/2007 | Callaway et al. ............... 442/304 |
| 2001/0008053 A1 | 7/2001 | Belli |
| 2001/0055994 A1 | 12/2001 | Kwitek |
| 2004/0048701 A1 | 3/2004 | Falone et al. |

FOREIGN PATENT DOCUMENTS

| | | |
|---|---|---|
| EP | 0374597 A | 6/1990 |
| GB | 458367 | 6/1935 |
| WO | 9100966 A | 1/1991 |
| WO | 03018144 A | 3/2003 |
| WO | 03032762 A | 4/2003 |
| WO | 03066174 A | 8/2003 |

* cited by examiner

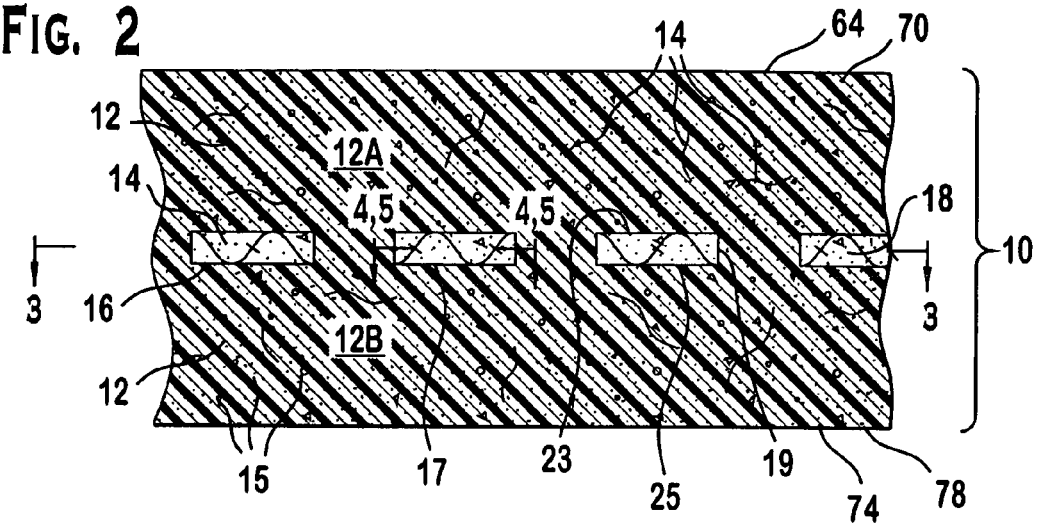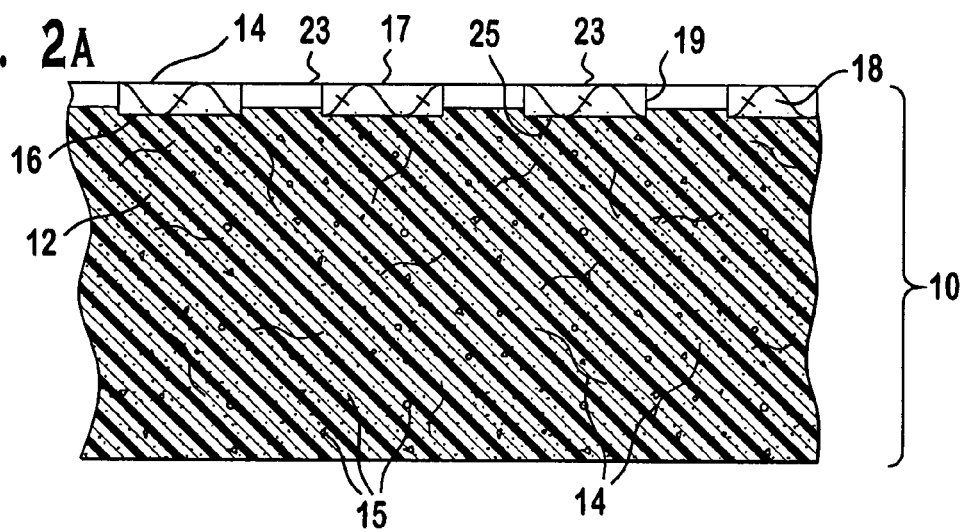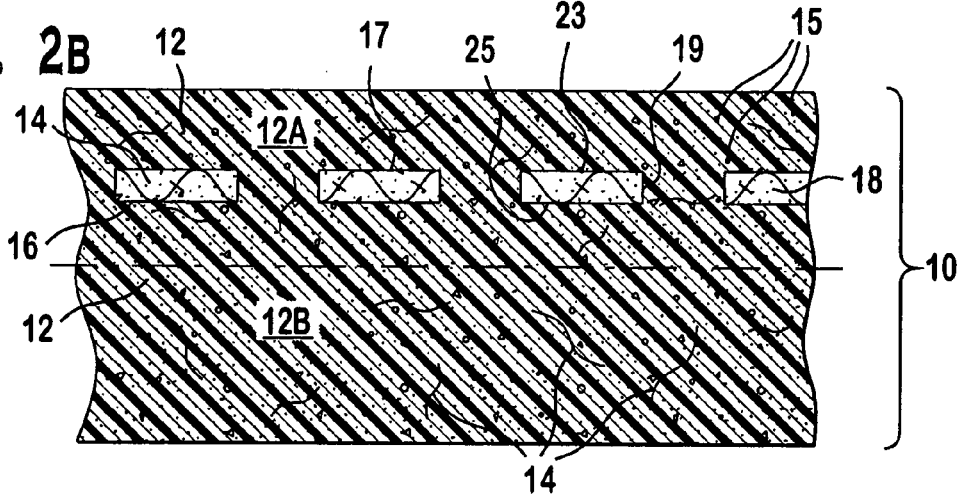

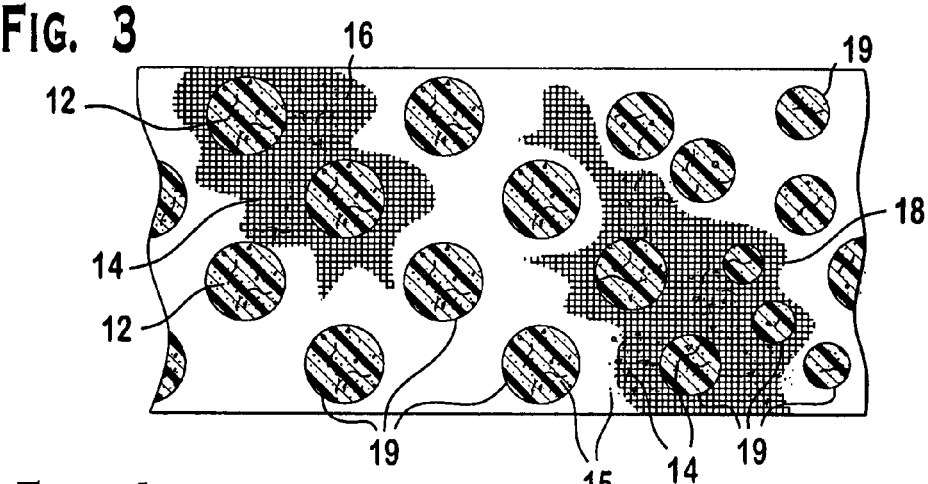
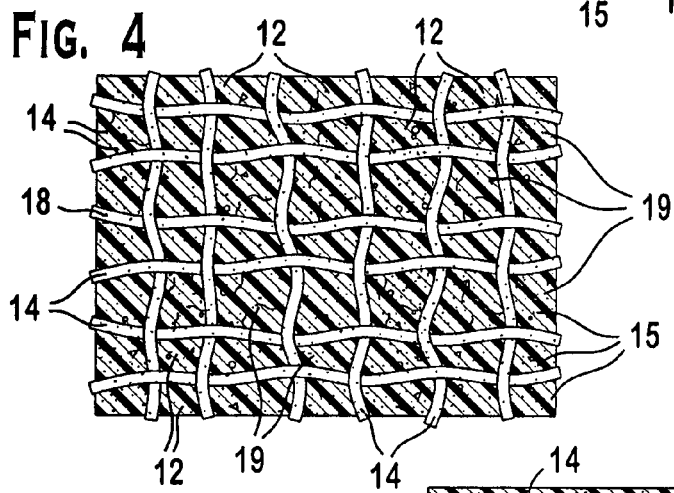
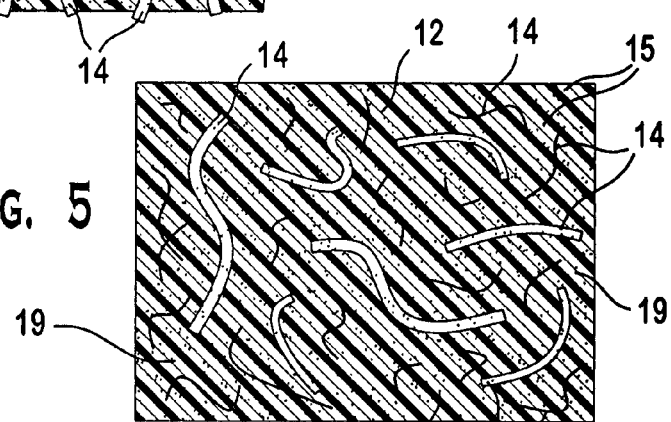
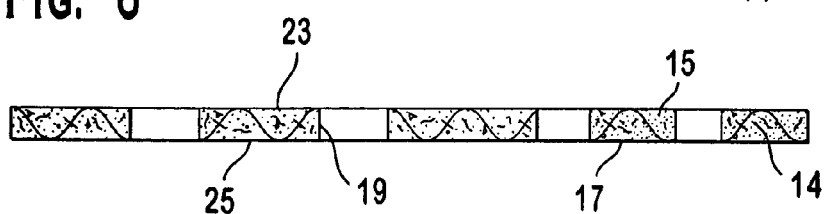

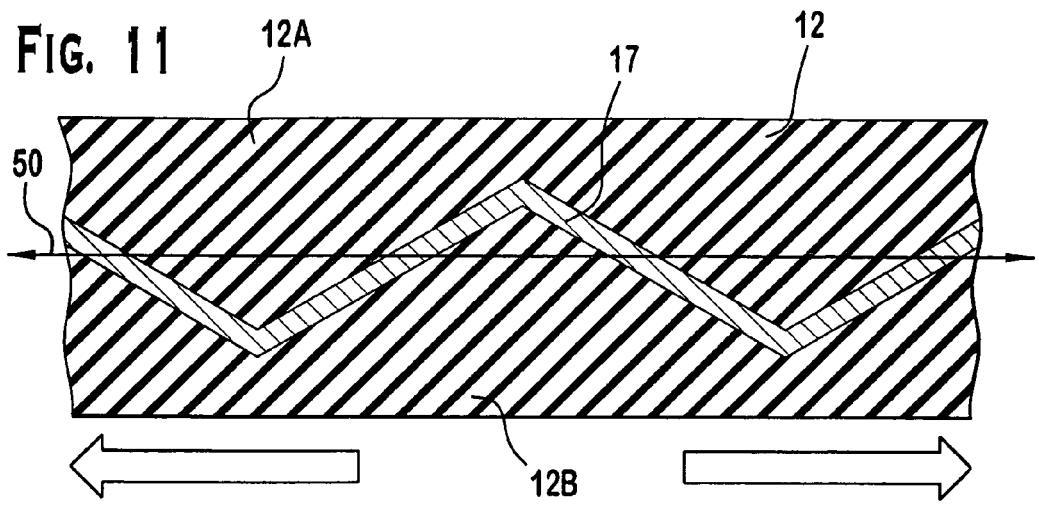
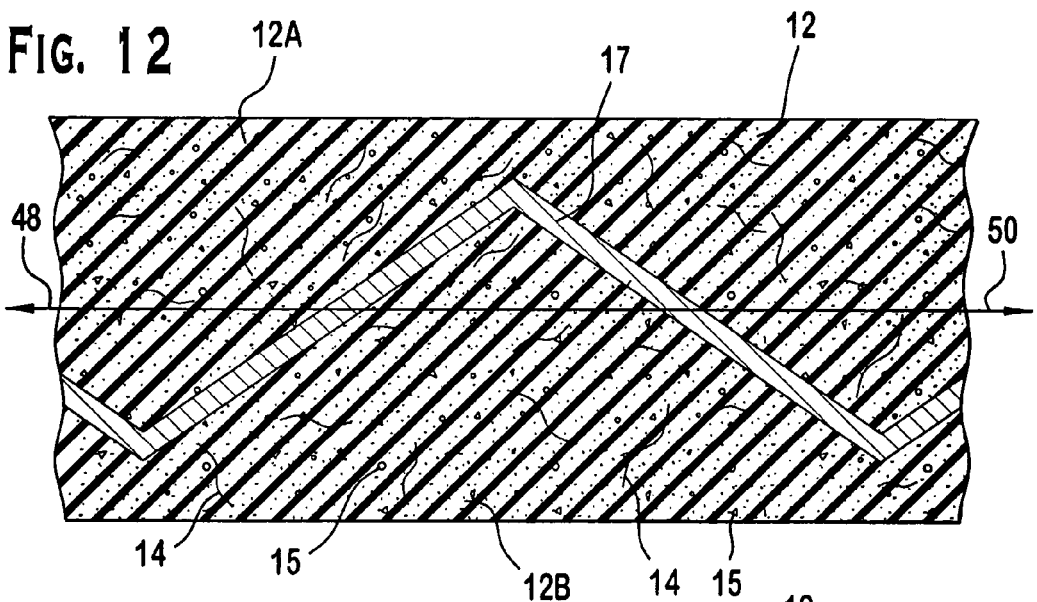
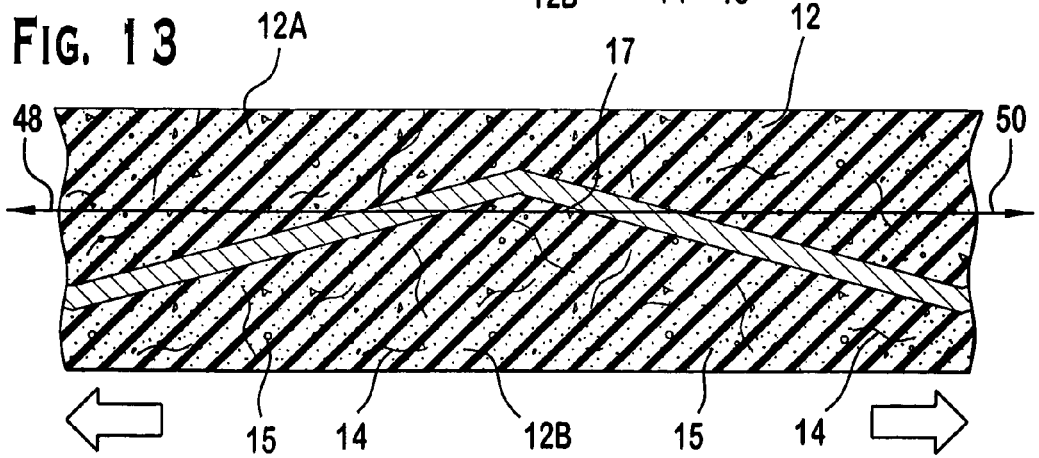

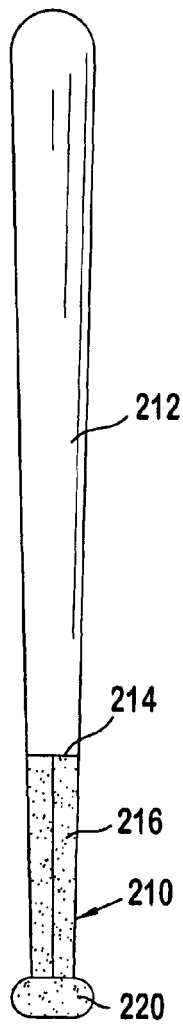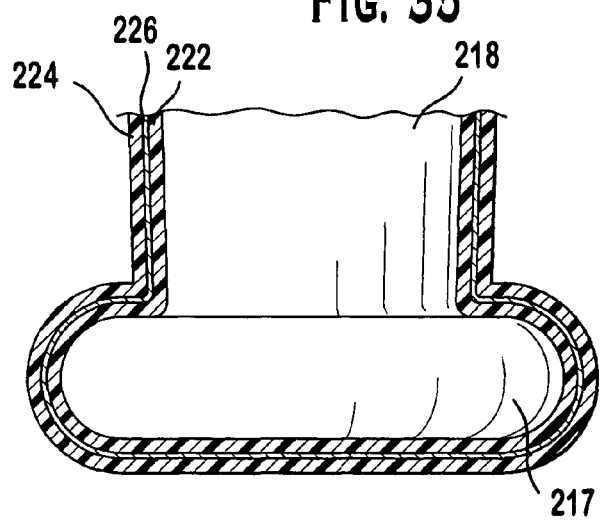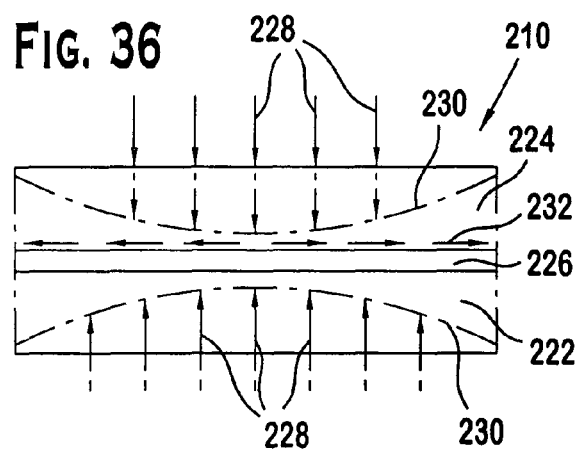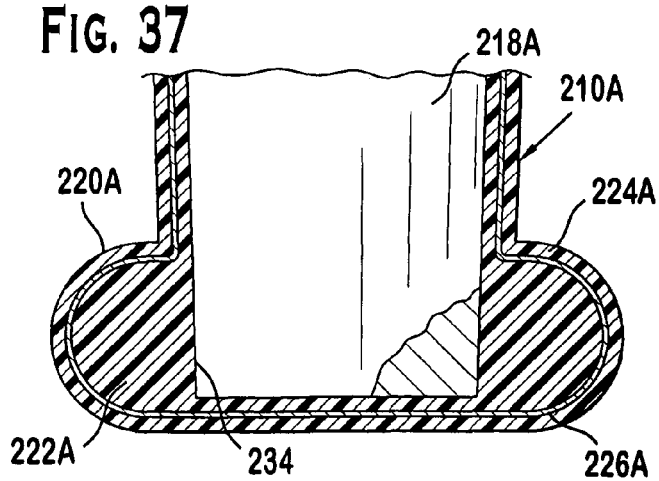

VIBRATION DAMPENING MATERIAL AND METHOD OF MAKING SAME

CROSS REFERENCE TO RELATED APPLICATION

This application is a continuation-in-part of U.S. Patent Application, currently pending, which is a continuation of and claims priority to U.S. patent application Ser. No. 10/659,560, currently pending, which is a divisional of and claims priority to U.S. patent application Ser. No. 09/939,319, filed on Aug. 27, 2001, now U.S. Pat. No. 6,652,398; priority to each of the above identified applications is claimed and each of the above identified applications are hereby incorporated by reference herein as if fully set forth in their entirety.

BACKGROUND

The present invention is directed to a material adapted to reduce vibration and, more specifically, to a method of making a material adapted to dissipate and evenly distribute vibrations acting on the material.

Handles of sporting equipment, bicycles, hand tools, etc. are often made of wood, metal or polymer that transmit vibrations that can make the items uncomfortable for prolonged gripping. Sporting equipment, such as bats, balls, shoe insoles and sidewalls, also transmit vibrations during the impact that commonly occurs during athletic contests. These vibrations can be problematic in that they can potentially distract the player's attention, adversely effect performance, and/or injure a portion of a player's body.

Rigid polymer materials are typically used to provide grips for tools and sports equipment. The use of rigid polymers allows users to maintain control of the equipment but is not very effective at reducing vibrations. While it is known that softer materials provide better vibration regulation characteristics, such materials do not have the necessary rigidity for incorporation into sporting equipment, hand tools, shoes or the like. This lack of rigidity allows unintended movement of the equipment encased by the soft material relative to a user's hand or body.

Additionally, injuries to the body can result in strained or sprained ligaments and bruised muscles or the like. Once an athlete has been injured it is necessary to support the injured portion of the athlete's body while minimizing the vibration experienced by the injured portion during further activity.

Prolonged or repetitive contact with excessive vibrations can injure a person. The desire to avoid such injury can result in reduced athletic performance and decreased efficiency.

Clearly what is needed is a method of making a material adapted to regulate vibration that provides the necessary rigidity for effective vibration distribution and for a user to maintain the necessary level of activity; and that can dampen and reduce vibrational energy.

SUMMARY

One embodiment of the present invention is directed to an athletic tape for wrapping a portion of a person's body. The athletic tape has a longitudinal axis and is adapted to provide a controlled support for the portion of the person's body. The athletic tape includes a tape body that is stretchable along the longitudinal axis from a first position to a second position, in which the tape body is elongated by a predetermined amount relative to the first position. The tape body includes a first elastomer layer defining a tape length, as measured along the longitudinal axis of the tape body. The support structure is disposed within the elastomer layer generally along the longitudinal axis in an at least partially non linear fashion while the tape body is in the first position so that a length of the support structure, as measured along a surface thereof, is greater than the tape length of the first elastomer layer. When the tape body is stretched into the second position, the support structure is at least partially strengthened out so that the support structure is more linear, relative to when the tape body is in the first position. The straightening of the support structure causes energy to be dissipated and generally prevents further elongation of the elastomer layer along the longitudinal axis past the second position. The support structure includes a plurality of fibers.

In another aspect, the present invention is directed to an athletic tape for wrapping a portion of a person's body. The athletic tape has a longitudinal axis and is adapted to provide a controlled support for the portion of the person's body. The athletic tape includes a tape body that is stretchable along the longitudinal axis from a first position to a second position, in which the tape body is elongated by a predetermined amount relative to the first position. The tape body includes a first elastomer layer that defines a tape length, as measured along the longitudinal axis, of the tape body. A support structure is disposed at least partially within the elastomer layer generally along the longitudinal axis in an at least partially non linear fashion while the tape body is in the first position so that a length of the support structure, as measured along a surface thereof, is greater than the tape length of the first elastomer layer. When the tape body is stretched into the second position, the support structure is at least partially straightened so that the support structure is more linear, relative to when the tape body is in the first position. The straightening of the support structure causes energy to be dissipated and generally prevents further elongation of the elastomer layer along the longitudinal axis past the second position.

In another aspect, the present invention is directed to a material having a stretch axis and that is adapted to regulate energy by distributing and partially dissipating energy exerted thereon. The material includes a material body that is elongateable along a stretch axis from a first position to a second position, in which the material is elongated by a predetermined amount relative to the first position. The material body includes a first elastomer layer defining a material length, as measured along the stretch axis, of the material body. A support structure is disposed within the elastomer layer generally along the stretch axis in an at least partially non linear fashion while the material body is in the first position so that a length of the support structure, as measured along a surface thereof, is greater than the material length of the first elastomer layer. When the material body is elongated into the second position, the support structure is at least partially straightened so that the support structure is more linear, relative to when the material body is in the first position. The straightening of the support structure causes energy to be dissipated and generally prevents further elongation of the elastomer layer along the stretch axis past the second position.

In another aspect, the present invention is directed to a padding for covering a portion of a person's body to provide support and/or impact for the portion. The padding has a stretch axis. The padding includes a padding body that is elongateable along the stretch axis from a first position to a second position, in which the padding body is elongated by a predetermined amount relative to the first position. The padding body includes a first elastomer layer that defines a padding length, as measured along the stretch axis, of the padding body. A support structure is disposed within the elastomer layer generally along the stretch axis in an at least partially non linear fashion while the padding body is in the first position so that a length of the support structure, as measured along a surface thereof, is greater than the padding length of the first elastomer layer. When the padding body is elongated into the second position, the support structure is at least partially straightened so that the support structure is more linear, relative to when the padding body is in the first position. The straightening of the support structure causes energy to be dissipated and generally prevents further elongation of the elastomer layer along the stretch axis past the second position.

In another aspect, the present invention is directed to a brace for wrapping a portion of a person's body. The brace has a stretch axis and is adapted to provide a controlled support for the portion of the person's body. The brace includes a brace body that is elongateable along the stretch axis from a first position to a second position in which the brace body is elongated by a predetermined amount relative to the first position. The brace body includes a first elastomer layer that defines a brace length, as measured along the stretch axis, of the brace body. A support structure is disposed within the elastomer layer generally along the stretch axis in an at least partially non linear fashion while the brace body is in the first position so that a length of the support structure, as measured along a surface thereof, is greater than the brace length of the first elastomer layer. When the brace body is stretched into the second position, the support structure is at least partially straightened so that the support structure is more linear, relative to when the brace body is in the first position. The straightening of the support structure causes energy to be dissipated and generally prevents further elongation of the elastomer layer along the stretch axis past the second position.

In another aspect, the present invention is directed to an athletic tape for wrapping a portion of a person's body. The athletic tape has a longitudinal axis and is adapted to provide a controlled support for the portion of the person's body. The athletic tape includes a tape body that is stretchable along the longitudinal axis from a first position to a second position, in which the tape body is elongated by a predetermined amount relative to the first position. The tape body includes a first elastomer layer that defines a tape length, as measured along the longitudinal axis of the tape body. A support structure is disposed over the elastomer layer and contacts the elastomer layer at a plurality of locations. The support structure extends generally along the longitudinal axis in an at least partially non linear fashion while the tape body is in the first position so that a length of the support structure, as measured along a surface thereof, is greater than the tape length of the first elastomer layer. When the tape body is stretched in the second position, the support structure is at least partially strengthened so that the support structure is more linear, relative to when the tape body is in the first position. The support structure includes a plurality of fibers.

BRIEF DESCRIPTION OF THE DRAWINGS

The foregoing summary, as well as the following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentality shown. In the drawings:

FIG. 2 is a cross-sectional view of the material of FIG. 1 separate from any implement, padding, equipment or the like;

FIG. 2A is a cross-sectional view of a second preferred embodiment of the material of the present invention with the support structure embedded thereon and the vibration dissipating material penetrating the support structure;

FIG. 2B is cross-sectional view of a third preferred embodiment of the material of the present invention with the support structure embedded within the vibration dissipating material and the vibration dissipating material penetrating the support structure, the support structure is positioned off center within the vibration dissipating material;

FIG. 3 is a cross-sectional view of a first preferred embodiment of the support structure as taken along the lines 3-3 of FIG. 2, the support structure is formed of polymer and/or elastomer and/or fibers, either of which may contain fibers, passageways extend through the support structure allowing the vibration dissipating material to penetrate the support structure;

FIG. 4 is cross-sectional view of a second preferred embodiment of the support structure as viewed in a manner similar to that of FIG. 3 illustrating a support structure formed by woven fibers, passageways through the woven fibers allow the support structure to be penetrated by the vibration dissipating material;

FIG. 5 is cross-sectional view of a third preferred support structure as viewed in a manner similar to that of FIG. 3; the support structure is formed by pluralities of fibers and particles; passageways past the fibers allow the vibration dissipating material to preferably penetrate the support structure;

FIG. 6 is a side elevational view of the support structure of FIG. 3;

FIG. 11 is a cross-sectional view of the material of FIG. 9 stretched along the longitudinal axis into a second position, in which the material body is elongated by a predetermined amount relative to the first position; the straightening of the support structure causes energy to be dissipated and preferably generally prevents further elongation of the material along the longitudinal axis past the second position;

FIG. 12 is a cross-sectional view of a third preferred embodiment of the material of the present invention illustrating a more linear support structure within the material while the material is in the first position; the more linear arrangement of the support structure in the material, relative to that shown in FIG. 9, reduces the amount of elongation that is possible before the material stops stretching and effectively forms a brake on further movement;

FIG. 13 is a cross-sectional view of the material of FIG. 12 stretched along the longitudinal axis into the second position, in which the material is elongated along the longitudinal axis by a predetermined amount; because the support structure was more linear while the material was in the first position, relative to the material shown in FIG. 11, it is preferred that the amount of elongation of the material when the material is in the second position is reduced relative to the material shown in FIGS. 9 and 11;

FIG. 19 also illustrates that a breakable layer (i.e., a paper layer) or a self fusing adhesive layer can be located on one surface of the material; when a self fusing layer is located on one surface of the material, the material can be wrapped so as to allow multiple adjacent wrappings of the material to fuse together to form an integral piece; if desired, the integral piece may be waterproof for use with swimming or the like;

FIG. 34 is an elevational view of a baseball bat having a cover in the form of a sleeve on the handle area in accordance with this invention;

FIG. 35 is an enlarged fragmental cross-sectional view of the bat and sleeve shown in FIG. 34;

FIG. 36 is a schematic diagram showing the results in the application of shock forces on a cover in accordance with this invention;

FIG. 37 is a view similar to FIG. 35 showing an alternative sleeve mounted on a different implement;

DETAILED DESCRIPTION OF THE PREFERRED EMBODIMENTS

Figure 1:
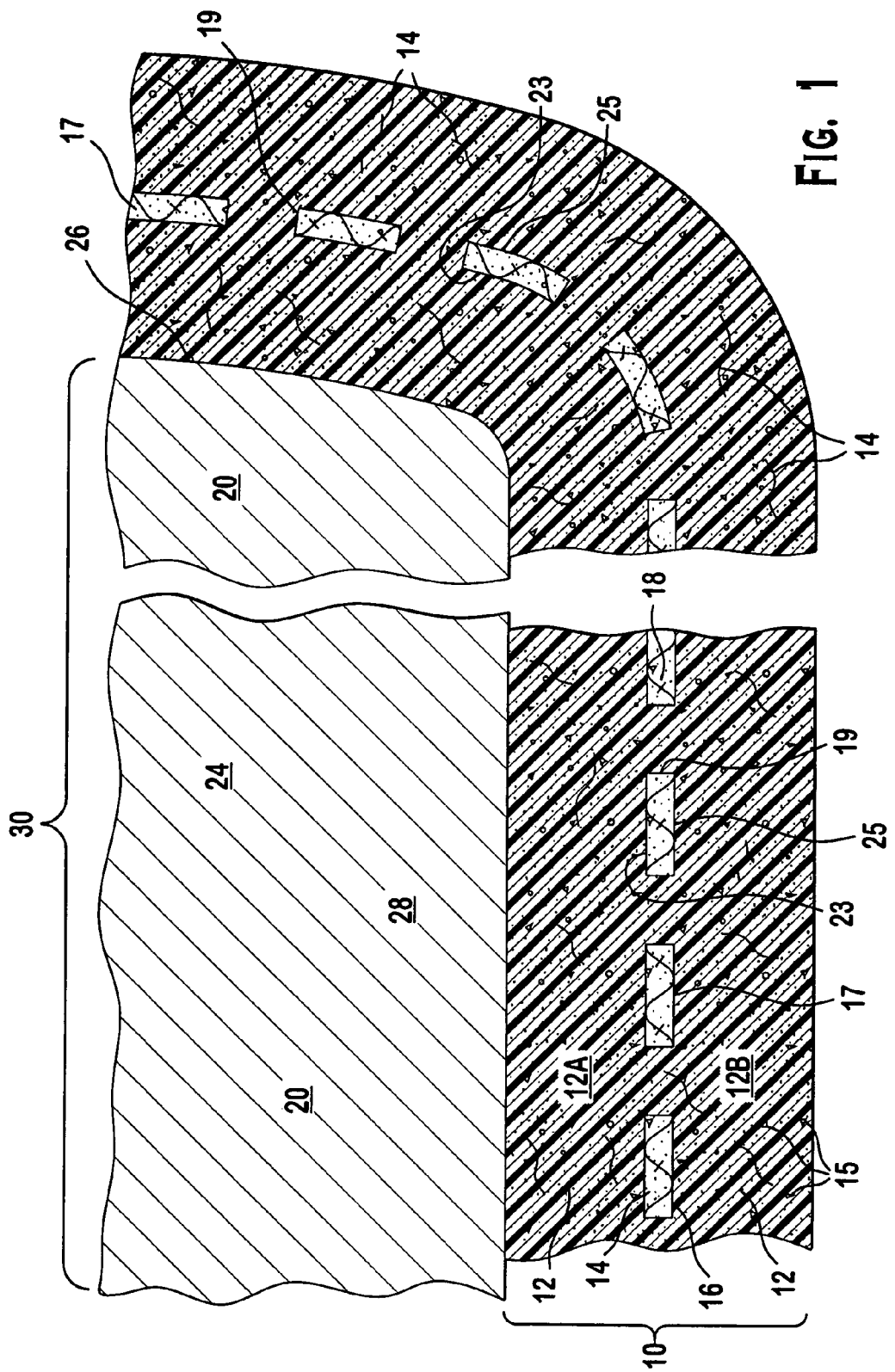
FIG. 1 is a cross-sectional view of a preferred embodiment of the material of the present invention illustrating a single layer vibration dissipating material with a support structure embedded therein, the material extends along a longitudinal portion of an implement and covers a proximal end thereof.

Certain terminology is used in the following description for convenience only and is not limiting. The words "right," "left," "top," and "bottom" designate directions in the drawings to which reference is made. The words "inwardly" and "outwardly" refer to directions toward and away from, respectively, the geometric center of the material and designated parts thereof. The term "implement," as used in the specification and in the claims, means "any one of a baseball bat, racquet, hockey stick, softball bat, sporting equipment, firearm, or the like." The term "particles," as used in the claims and in the corresponding portions of the specification, means "small bits or pieces of mass each defining a volume but generally being of insufficient, length to interweave together." Additionally, the words "a" and "one" are defined as including one or more of the referenced item unless specifically stated otherwise. The above terminology includes the words above specifically mentioned, derivatives thereof, and words of similar import.

Referring to FIGS. 1-33, wherein like numerals indicate like elements throughout, there are shown preferred embodiments of a material, generally designated 10, that is adapted to regulate vibration. Briefly stated, the material 10 preferably includes a vibration dissipating material 12 (preferably an elastomer layer). One embodiment of the vibration dissipating material 12 penetrates a support structure 17 to embed the support structure 17 thereon (as shown in FIG. 2A) and/or therein (as shown in FIG. 2B). The support structure 17 is preferably semi-rigid (but can be rigid without departing from the scope of the present invention) and supports the vibration dissipating material 12. The support structure can be formed by a second elastomer layer of same or differing rigidity.

The material 10 of the present invention was the result of extensive research and was thoroughly tested by Villanova University's Department of Mechanical Engineering by a professor having a Ph.D. in vibratory physics. Testing of the material 10 determined that the material 10 can reduce the magnitude of sensible vibration by eighty (80%) percent. The material 10 has verified, superior vibration dissipation properties due to the embedded support structure 17 that is located on and/or in the elastomer 12. In addition to evenly distributing vibration, the support structure 17 contributes to the absorption of vibration and supports the vibration dissipating material 12 to prevent the layer of vibration dissipating material 12 from twisting or otherwise becoming unsuitable for use as a grip or padding.

While it is preferred that the vibration dissipating material layer 12 be formed by elastomer, those of ordinary skill in the art will appreciate from this disclosure that the vibration dissipating material 12 can be formed by any suitable polymer without departing from the scope of the present invention. For clarity only, the vibration dissipating material 12 will be often described herein as being an elastomer without any mention of the material possibly being a polymer. However, it should understood that even when the layer 12 is only described as being an elastomer, that the present invention also includes the material 12 being a any suitable polymer.

The material 10 of the present invention can be incorporated into athletic gear, grips for sports equipment, grips for tools, and protective athletic gear. More specifically, the material 10 can be used: to form grips for a tennis racquet, hockey sticks, golf clubs, baseball bats or the like; to form protective athletic gear for mitts, headbands, mouth guards, face protection devices, helmets, gloves, to form athletic tape, to form braces, to form molded wraps for a portion of a person's body, to form pads, exercise pads, elevator pads, padding that is stood on, padding that is wrapped around objects to protect people from injury when colliding with such objects, padding that is worn for fashion, padding that is worn to ameliorate tennis elbow, padding that is used to support gun butts, padding that is used to support bullet proof vests, hip pads, shoulder pads, chest protectors, or the like; to form seats or handle bar covers for bicycles, motorcycles, or the like; to form boots for skiing, roller blading or the like; to form footwear, such as shoe soles and inserts; to form grips for firearms, hand guns, rifles, shotguns, or the like; and to form grips for tools such as hammers, drills, circular saws, chisels or the like.

The elastomer layer 12 acts as a shock absorber by converting mechanical vibrational energy into heat energy. The embedded support structure 17 redirects vibrational energy and provides increased stiffness to the material 10 to facilitate a user's ability to control an implement 20 encased, or partially encased, by the material 10. The elastomer layer 12, 12A, or 12B may include a plurality of fibers 14 (further described below) or a plurality of particles 15 (further described below). The incorporation of the support structure 17 on and/or within the material 10 allows the material 10 to be formed by a single elastomer layer without the material 10 being unsuitable for at least some of the above-mentioned uses. The support structure 17 may also include a plurality of fibers 14 or a plurality of particles 15. However, those of ordinary skill in the art will appreciate from this disclosure that additional layers of material can be added to any of the embodiments of the present invention disclosed below without departing from the scope of the invention.

In the situation where the support structure 17 is formed by a second elastomer layer, the two elastomer layers can be secured together via an adhesive layer, discreet adhesive locations, or using any other suitable method to secure the layers together. Regardless of the material used to form the support structure 17, the support structure is preferably located and configured to support the first elastomer layer (see FIGS. 1-2B).

It is preferred that the material 10 have a single contiguous elastomer body 12. Referring to FIG. 1, the support structure has first and second major surfaces 23, 25. In one embodiment, the elastomer 12 extends through the support structure 17 so that the portion of the elastomer 12A contacting the first major support structure surface 23 (i.e., the top of the support structure 17) and the portion of the elastomer 12B contacting the second major support structure surface 25 (i.e., the bottom of the support structure) form the single contiguous elastomer body 12. Elastomer material provides vibration damping by dissipating vibrational energy. Suitable elastomer materials include, but are not limited, urethane rubbers, silicone rubbers, nitrile rubbers, butyl rubbers, acrylic rubbers, natural rubbers, styrene-butadiene rubbers, and the like. In general, any suitable elastomer or polymer material can be used to form the vibration dissipating layer 12.

The softness of elastomer materials can be quantified using Shore A durometer ratings. Generally speaking, the lower the durometer rating, the softer the material and the more effective a material layer is at absorbing and dissipating vibration because less force is channeled through the material. When a soft material is squeezed, an individual's fingers are embedded in the material which increases the surface area of contact between the user's hand and creates irregularities in the outer material surface to allow a user to firmly grasp any implement 20 covered, or partially covered, by the material. However, the softer the material, the less control a user has when manipulating an implement 20 covered by the material. If the elastomer layer is too soft (i.e., if the elastomer layer has too low of a Shore A Durometer rating), then the implement 20 may rotate unintentionally relative to a user's hand or foot. The material 10 of the present invention is preferably designed a Shore A durometer rating that provides an optimum balance between allowing a user to precisely manipulate and control the implement 20 and effectively damping vibration during use of the implement 20 depending on the activity engaged in.

It is preferable, but not necessary, that the elastomer used with the material 10 have a Shore A durometer of between approximately ten (10) and approximately eighty (80). It is more preferred that the elastomer 12 have a Shore A durometer of between approximately fifteen (15) and approximately forty-five (45).

The elastomer 12 is preferably used to absorb vibrational energy and to convert vibrational energy into heat energy. The elastomer 12 also provides a compliant and comfortable grip for a user to grasp (or provides a surface for a portion of a user's body, such as the under sole of a user's foot when the material 10 is formed as a shoe insert).

In one embodiment, the material 10 preferably has a Shore A durometer of approximately fifteen (15). In another embodiment, the material 10 preferably has a Shore A Shore Durometer of approximately forty two (42). In yet another embodiment, the material 10 preferably has a Shore A Durometer of approximately thirty-two (32). Of course, those of ordinary skill in the art will appreciate that the Shore A Durometer of the material 10 can varied without departing from the scope of the present invention.

Referring to FIGS. 3-5, the support structure 17 can include any one (or combination of) of a polymer, an elastomer, particles, a plurality of fibers, a plurality of woven fibers, a cloth, and a plurality of cloth layers. If the support structure 17 and the layer 12 are both polymers or both elastomers, then they can be the same or different from each other without departing from the scope of the present invention. If vibration dissipating material 12 is formed of the same material as the support structure 17, then the support structure 17 can be made more rigid than the main layer 12 by embedding fibers 14 therein. It is preferable that the support structure 17 is generally more rigid than the vibration dissipating material 12.

Referring specifically to FIG. 3, the support structure 17 may be formed of an elastomer that may but does not necessarily, also have fibers 14 embedded therein (examplary woven fibers are shown throughout portions of FIG. 3). Referring to FIG. 4, the support structure 17 may be formed by a plurality of woven fibers 18. Referring to FIG. 5, the support structure 17 may be formed by a plurality of fibers 14. Regardless of the material forming the support structure 17, it is preferable that passageways 19 extend into the support structure 17 to allow the elastomer 12 to penetrate and embed the support structure 17. The term "embed," as used in the claim and in the corresponding portions of the specification, means "contact sufficiently to secure thereon and/or therein." Accordingly, the support structure 17 shown in FIG. 2 A is embedded by the elastomer 12 even though the elastomer 12 does not fully enclose the support structure 17. Additionally, as shown in FIG. 2 B, the support structure 17 can be located at any level or height within the elastomer 12 without departing from the scope of the present invention. While the passageways 19 are shown as extending completely through the support structure 17, the invention includes passageways 19 that extend partially through the support structure 17.

Referring again to FIG. 2A, in one embodiment, it is preferred that the support structure 17 be embedded on the elastomer 12, with the elastomer penetrating the support structure 17. The support structure 17 being generally along a major material surface 38 (i.e., the support structure 17 is generally along the top of the material).

The fibers 14 are preferably, but not necessarily, formed of high tensile fibrous material (one example of which are aramid fibers). However, the fibers can be formed from any one or combination of the following: bamboo, glass, metal, elastomer, polymer, ceramics, corn husks, and/or any other renewable resource. By using fibers from renewable resources, production costs can be reduced and the environmental friendliness of the present invention can be increased. Referring to FIG. 4, the fibers 14 can be woven to form a cloth 16 that is disposed on and/or within the elastomer 12. Multiple cloth layers 16 can be epoxied or otherwise secured together and incorporated into the support structure 17. The cloth layer 16 can be formed of woven aramid fibers or other types of fiber. The aramid fibers 14 block and redirect vibrational energy that passes through the elastomer 12 to facilitate the dissipation of vibrations. The aramid fibers 18 redirect vibrational energy along the length of the fibers 18. Thus, when the plurality of aramid fibers 18 are woven to form the cloth 16, vibrational energy emanating from the implement 20 that is not absorbed or dissipated by the elastomer layer 12 is redistributed evenly along the material 10 by the cloth 16 and preferably also further dissipated by the cloth 16.

It is preferable that the aramid fibers 18 are formed of a suitable polyamide fiber of high tensile strength with a high resistance to elongation. However, those of ordinary skill in the art will appreciate from this disclosure that any aramid fiber suitable to channel vibration can be used to form the support structure 17 without departing from scope of the present invention. Additionally, those of ordinary skill in the art will appreciate from this disclosure that loose aramid fibers or chopped aramid fibers can be used to form the support structure 17 without departing from the scope of the present invention. The fibers may also be formed of fiberglass or the like.

When the aramid fibers, or any high tensile fibrous material, 18 are woven to form the cloth 16, it is preferable that the cloth 16 include at least some floating aramid fibers 18. That is, it is preferable that at least some of the plurality of aramid fibers 18 are able to move relative to the remaining aramid fibers 18 of the cloth 16. This movement of some of the aramid fibers 18 relative to the remaining fibers of the cloth converts vibrational energy to heat energy.

Particles 15 can be located in either an elastomer layer 12, 12A, and/or 12B and/or in the support structure 15. The particles 15 increase the vibration absorption of the material of the present invention. The particles 15 can be formed of pieces of glass, polymer, elastomer, chopped aramid, ceramic, chopped fibers, sand, gel, foam, metal, mineral, glass beads, or the like. Gel particles 15 provide excellent vibration dampening due their low durometer rating. One exemplary gel that is suitable for use the present invention is silicone gel. However, any suitable gel can be used without departing from the present invention.

The material 10 may be configured and adapted to form an insert for shoe. When the material 10 is configured to form a shoe insert, the material 10 is preferably adapted to extend along an inner surface of the shoe from a location proximate to a heel of the shoe to the toe of the shoe. In addition to forming a shoe insert, the material 10 can be located along the sides and top of the shoe to protect the wearer's foot from lateral and vertical impacts.

Figures 7, 8:
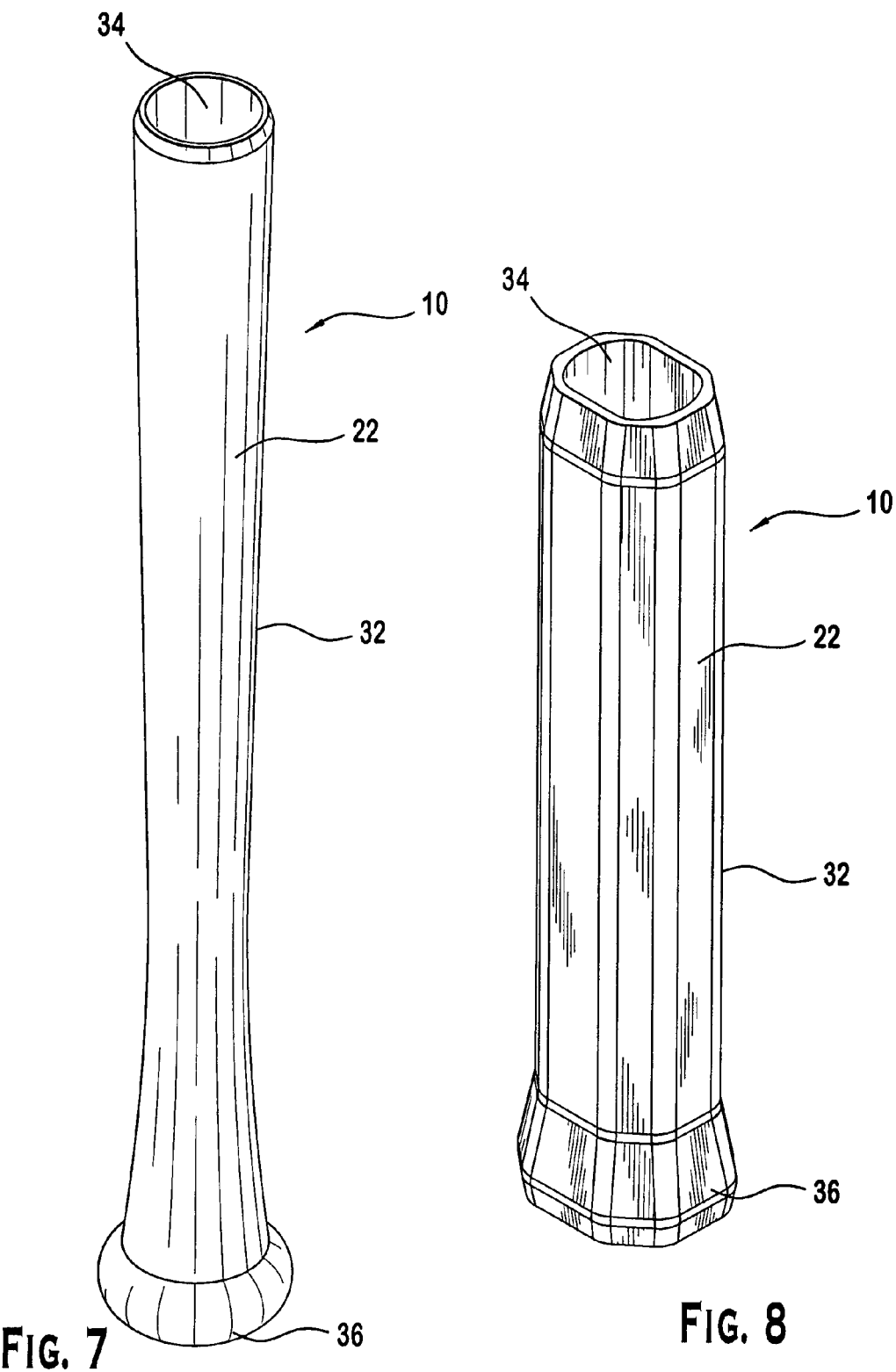
FIG. 7 is perspective view of the material of FIG. 1 configured to form a grip for a bat.
FIG. 8 is perspective view of the material of FIG. 1 configured to form a grip for a racquet.

The material 10 may be configured and adapted to form a grip 22 for an implement such as a bat, having a handle 24 and a proximal end 26 (i.e., the end near to where the bat is normally gripped). The material 10 is preferably adapted to enclose a portion of the handle 24 and to enclose the proximal end 26 of the bat or implement 20. As best shown in FIGS. 7 and 8, it is preferable that the grip 22 be formed as a single body that completely encloses the proximal end of the implement 20. The material 10 may be also be configured and adapted to form a grip 22 for a tennis racket or similar implement 20 having a handle 24 and a proximal end 26.

While the grip 22 will be described below in connection with a baseball or softball bat, those of ordinary skill in the art will appreciate that the grip 22 can be used with any of the equipment, tools, or devices mentioned above without departing from the scope of the present invention.

When the grip 22 is used with a baseball or softball bat, the grip 22 preferably covers approximately seventeen (17) inches of the handle of the bat as well as covers the knob (i.e., the proximal end 26 of the implement 20) of the bat. The configuration of the grip 22 to extend over a significant portion of the bat length contributes to increased vibrational damping. It is preferred, but not necessary, that the grip 22 be formed as a single, contiguous, one-piece member.

Referring to FIG. 1, the baseball bat (or implement 20) has a handle 24 including a handle body 28 having a longitudinal portion 30 and a proximal end 26. The material 10 preferably encases at least some of the longitudinal portion 30 and the proximal end 26 of the handle 24. The grip material 10 can incorporate any of the above-described support structures 17. The aramid fiber layer 14 is preferably formed of woven aramid fibers 18.

As best shown in FIGS. 7 and 8, the preferred grip 22 is adapted for use with an implement 20 having a handle and a proximal handle end. The grip 22 includes a tubular shell 32 having a distal open end 34 adapted to surround a portion of the handle and a closed proximal end 36 adapted to enclose the proximal end of the handle. It is preferable not necessary, that the material completely enclose the proximal end 26 of the handle. The tubular shell 32 is preferably formed of the material 10 which dissipates vibration.

Multiple methods can be used to produce the composite or multi-layer material 10 of the present invention. Briefly speaking, one method is to extrude the material 10 by pulling a support structure 17 from a supply roll while placing the elastomer layer on both sides of the support structure 17. It is preferred, but not necessary, that the particles 15 in either of the support structure 17 or the elastomer layer are already located in their respective material on the appropriate supply roll. A second method of producing the material 10 of the present invention is to weave a fiber onto the implement 20 and then to mold the elastomer 12 thereover. Alternatively, a support structure can be pressure fit to an elastomer to form the material 10. Those of ordinary skill in the art will appreciate from this disclosure that any other known manufacturing methods can be used to form the material 10 without departing from the scope of the present invention. Any of the below described methods can be used to form a material 10 or grip 22 having any of the above specified Shore A Durometers and incorporating any of the above-described support structures 17.

More specifically, one preferred method of making the material 10 includes:

providing an uncured elastomer 12. A cloth layer is positioned on and/or within the uncured elastomer 12. The cloth layer is formed by a plurality of woven aramid fibers 14. The uncured elastomer 12 penetrates the cloth layer 16 to embed to the cloth 16. The uncured elastomer 12 is at least partially cured to form the material 10. The cloth layer 16 supports the cured elastomer 12 and facilitates the distribution and dissipation of vibration by the material 10.

It is preferable that the elastomer 12 is cured so that some of the plurality of aramid fibers in the cloth layer 16 are able to move relative to the remaining plurality of aramid fibers 18. It is also preferable that the material 10 be configured to form a grip for a bat and/or racquet having a handle 24 and the proximal end 26. The grip 22 preferably encloses at least a portion of the handle 24 and the proximal end 26.

Another aspect of the present invention is directed to a method of making a grip 22 for an implement 20 having a handle 24 and a proximal end 26. The grip 22 is formed by a single layer material 10 adapted to regulate vibration. The method includes providing an uncured elastomer. A plurality of fibers 14 are positioned on and/or within the uncured elastomer 12. The uncured elastomer 12 is at least partially cured to form the single layer material embedding the plurality of fibers. The single layer material 10 has first and second major material surfaces. The single layer material 10 is positioned over at least a portion of the handle 24 and over the proximal end 26 of the handle 24. The first major material surface contacts the implement 20 and second major material surface of the single layer material 10 forms a surface for a user to grasp. This method can be used to form a grip 22 having any of the Shore A Durometers described above and can use any of the support structure 17 also described above.

In another aspect, the present invention is directed to a method of making a material 10 adapted to regulate vibration. The method includes providing a cloth 16 formed by a plurality of woven aramid fibers 14. The cloth has first and second major surfaces. A first elastomer layer 12A is placed on the first major surface of the cloth. A second elastomer layer 12B is placed on the second major surface 25 of the cloth 16. The first and second elastomer layers 12A, 12B penetrate the cloth 16 to form a single layer elastomer 12 having an embedded cloth 16 for support thereof.

In another aspect, the present invention is directed to a method of forming a material 10 including providing a cloth layer 16. Positioning an elastomer 12 substantially over the cloth layer 16. Applying pressure to the cloth layer 16 and the elastomer 12 to embed the cloth layer 16 on and/or in the elastomer 12 to form the material 10. When using this sort of pressure fit technique, those ordinary skill in the art will appreciate from this disclosure that the cloth layer 16 and the elastomer 12 can be placed in a mold prior to applying pressure without departing from the scope of the present invention.

The covering of the proximal end of an implement 20 by the grip 22 results in reduced vibration transmission and in improved counter balancing of the distal end of the implement 20 by moving the center of mass of the implement 20 closer to the hand of a user (i.e., closer to the proximal end 26). This facilitates the swinging of the implement 20 and can improve sports performance while reducing the fatigue associated with repetitive motion.

In addition to use with implements or as covers, the material shown in FIGS. 1-6 can be used as: an athletic tape, padding, bracing material, or the like (as shown in FIGS. 24-33) without departing from the scope of the present invention. Referring to FIGS. 2-9, and 12; an athletic tape for wrapping a portion of a person's body; a material having a stretch axis and being adapted to regulate energy by disputing and partially dissipating energy exerted thereon; a padding for covering a portion of a person's body or an object; and/or a brace for wrapping a portion of a person's body is shown. For simplicity, the material 10 will be initially described in connection with athletic tape, but those of ordinary skill in the art will appreciate from this disclosure that the material 10 can be used in any of the above described applications or in any other application where vibration absorption or having a controlled material stretch is desired.

When the material of the present invention is used to form athletic tape, that athletic tape provides a controlled support for a portion of the person's body. The athletic tape includes a tape body 64 that is preferably stretchable along a longitudinal axis 48 (or stretch axis 50) from a first position to a second position, in which the tape body 64 is elongated by a predetermined amount relative to the first position.

Figure 9:
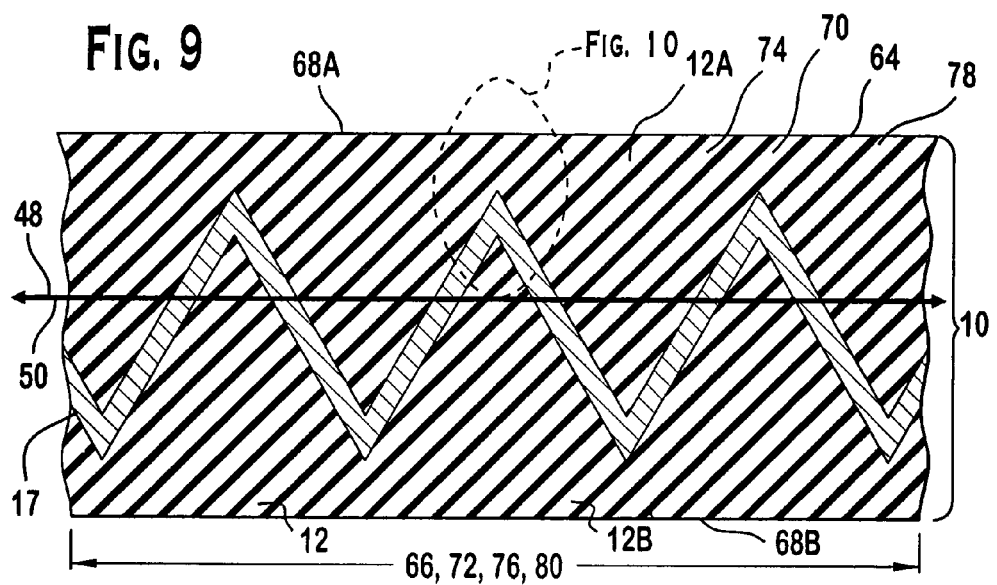
FIG. 9 is a cross-sectional view of a second preferred embodiment of the material of the present invention illustrating a single layer of vibration dissipating material with a support structure embedded therein; the support structure is disposed within the vibration dissipating material generally along a longitudinal axis in an at least partially non linear fashion so that a length of the support structure, as measured along a surface thereof, is greater than the length of the vibration dissipating material as measured along the longitudinal axis, of the material body.

FIGS. 9 and 11 illustrate a second preferred embodiment of the material of the present invention in the first and second positions, respectively. FIGS. 12 and 13 illustrate a third preferred embodiment of the material of the present invention in the first and second positions, respectively.

As described below, the configuration of the support structure 17 within the vibration absorbing layer 12 allows the predetermined amount of elongation to be generally fixed so that the athletic tape provides a controlled support that allows limited movement before applying a brake on further movement of the wrapped portion of a person's body. This facilitates movement of a wrapped joint while simultaneously dissipating and absorbing vibration to allow superior comfort and performance as compared to that experienced with conventional athletic tape. While the predetermined amount of elongation can be set to any value, it is preferably less than twenty (20%) percent. The predetermined amount of elongation is more preferably less than two (2%) percent. However, depending on the application any amount of elongation can be used with the material 10 of the present invention.

The tape body 64 preferably includes a first elastomer layer 12 that defines a tape length 66, as measured along the longitudinal axis 48, of the tape body 64. The support structure 17 is preferably disposed within the elastomer layer 12 generally along the longitudinal axis 48 in an at least partially non linear fashion while the tape body is in the first position so that a length of the support structure 17, as measured along a surface thereof, is greater than the tape length 66 of the first elastomer layer 12. It is preferred, by not necessary, that the support structure 17 (or ribbon material) is positioned in a generally sinusoidal fashion within the elastomer layer 12 while the tape body 64 is in the first position. However, the support structure 17 can be positioned in an irregular fashion without departing from the scope of the present invention. As described above, the support structure 17 and/or the elastomer layer 12 can include particles, fibers, or the like (as shown in FIGS. 12 and 13).

Referring to FIGS. 11 and 13, when the tape body 64 is stretched into the second position, the support structure 17 is preferably at least partially straightened so that the support structure 17 is more linear (or in case of the material shown in FIG. 2, the support structure 17 would likely be thinner), relative to when the tape body 64 is in the first position (as shown in FIGS. 2, 9, and 12). The straightening of the support structure causes energy to be dissipated and preferably generally prevents further elongation of the elastomer layer 12 along the longitudinal axis 48 past the second position. Energy dissipation occurs due to the stretching of the material of the support structure 17 and can occur due to the separation or partial pulling away of the support structure 17 from the attached elastomer layer 12.

Figure 10:
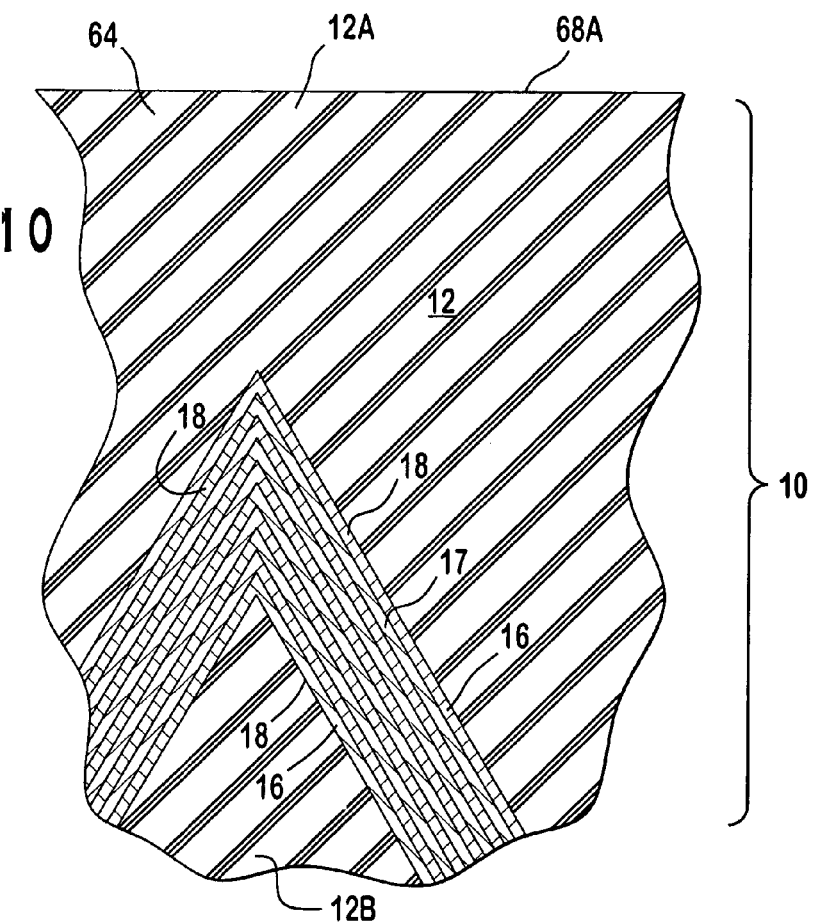
FIG. 10 is an enlarged broken away view of the area enclosed by the dashed lines labeled "FIG. 10" in FIG. 9 and illustrates that the "overall support structure" can actually be formed by a plurality of individual stacked support structures (which can be the same or different from each other) or a successive plurality of stacked fibers and/or a successive plurality of stacked cloth layers.

Referring to FIG. 10, the "overall support structure" 17 may comprise a plurality of stacked support structures, fibers 18, and/or cloth layers 16. It is preferred that the plurality of fibers include aramid fibers or other high tensile strength fibrous material. Alternatively, the plurality of fibers may be formed of fiberglass material or be woven into a ribbon or cloth. Additionally, as described above in connection with FIGS. 2-6, the support structure can include any one (or combination) of a polymer, an elastomer, particles; fibers; woven fibers; a cloth; a plurality of cloth layers; loose fibers, chopped fibers, gel particles, particles, sand, or the like without departing from the scope of the present invention.

As detailed above, the support structure 17 and/or the elastomer layer 12 may include a plurality of particles therein. Such particles may include any one or combination of gel particles, sand particles, glass beads, chopped fibers, metal particles, foam particles, sand, or any other particle in parting desirable vibration dissipation characteristics to the material 10.

Figure 19:
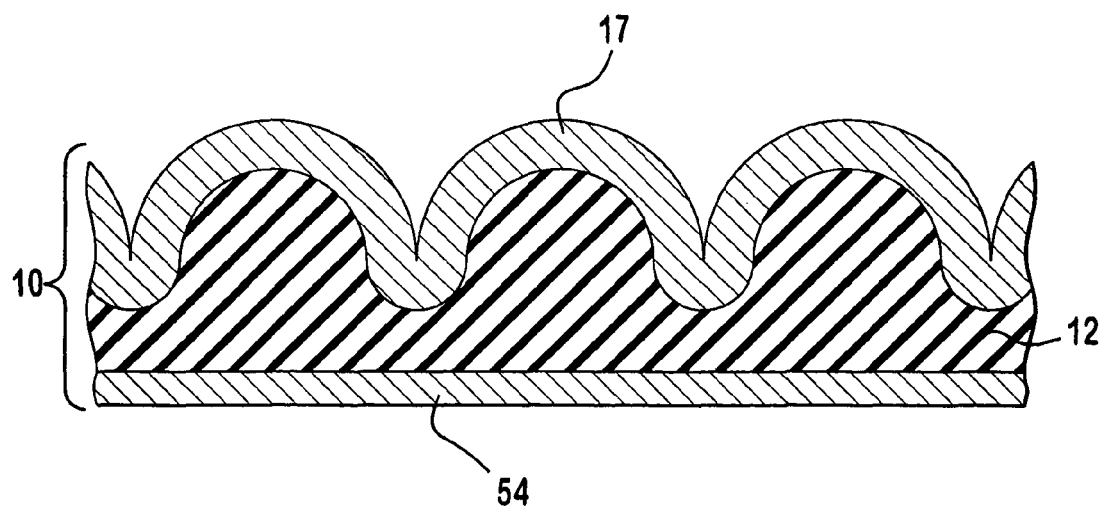
FIG. 19 is a cross-sectional view of a ninth preferred embodiment of the material of the present invention and illustrates that the support structure can be positioned generally along an outer surface of the vibration dissipating material without departing from the scope of the present invention.
Figure 20:
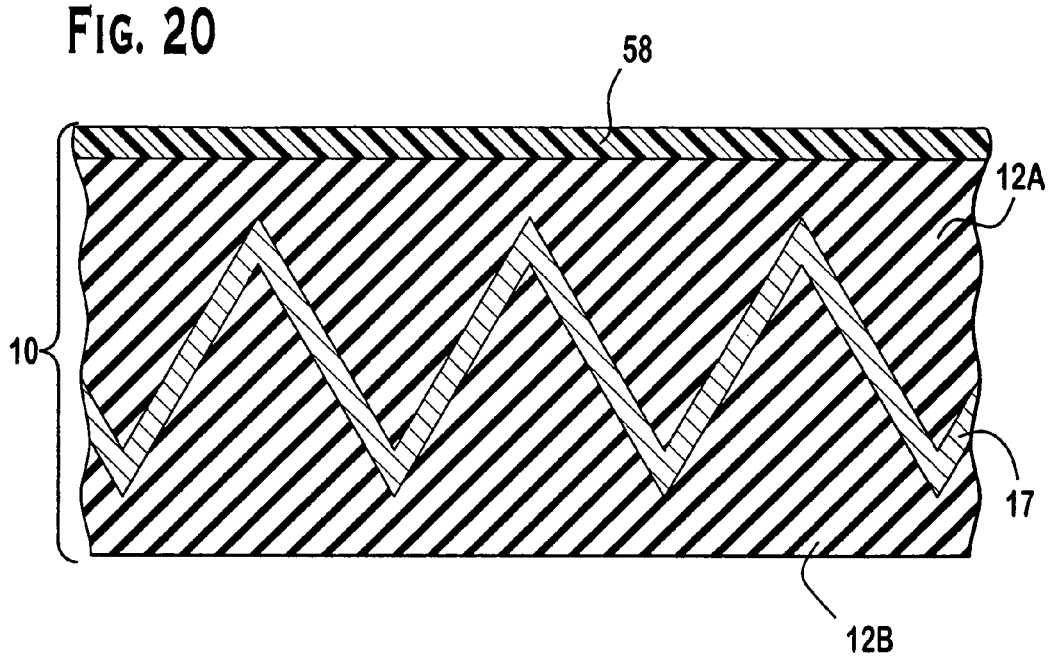
FIG. 20 is a cross-sectional view of a tenth preferred embodiment of the vibration dissipating material with a shrinkable layer of material disposed on a major surface thereof; the shrinkable material can be a heat shrinkable material or any other type of shrinking material suitable for use with the present invention; once the material is properly positioned, the shrinkable layer can be used to fix the material in position and, preferably, can also be used as a separate breakable layer to further dissipate vibration in a fashion similar to the breakable layer described in connection with FIG. 17.
Figure 21:
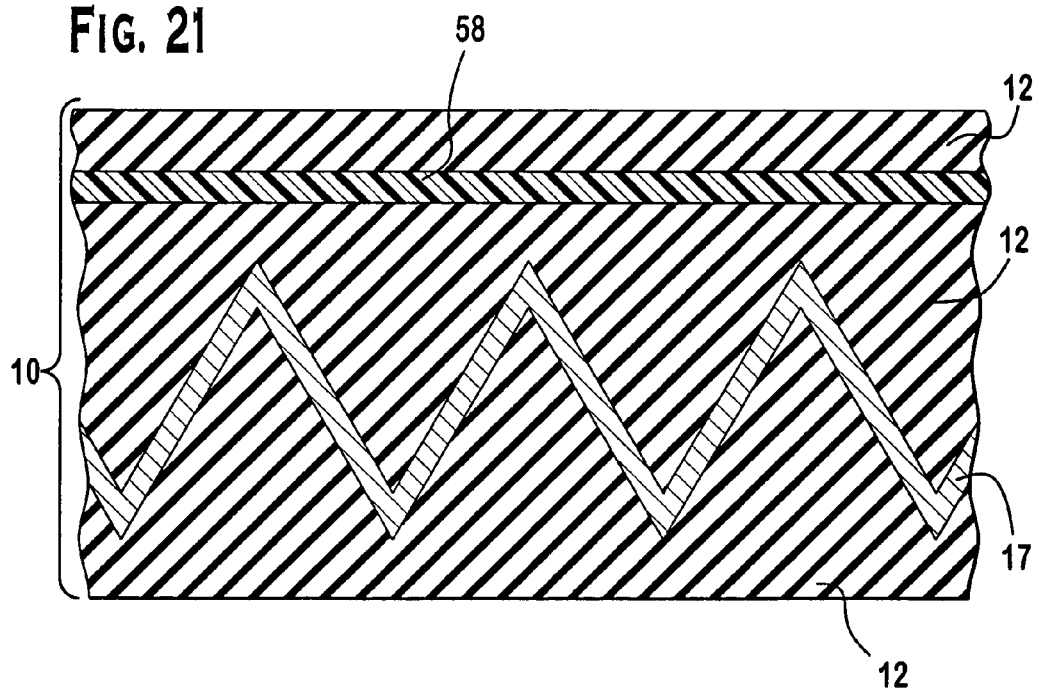
FIG. 21 is an eleventh preferred embodiment of the vibration dissipating material of the present invention and illustrates the shrinkable layer disposed within the vibration dissipating material; the shrinkable layer can be a solid layer, a perforated layer, a mesh or netting, or shrinkable fibers.

Referring to FIGS. 9 and 10, it is preferred that the tape body 64 have top and bottom surfaces 68A, 68B, respectively. The bottom surface 68B faces the portion of the person's body when the athletic tape 10 is wrapped thereover. When the support structure 17 is formed by a plurality of fibers 18, it is preferable that the plurality of fibers 18 define multiple stacked fiber layers between the top and bottom surfaces 68A, 68B. It is preferable that the plurality of fibers 18 are stacked between four (4) and sixteen (16) times between the top and bottom surfaces 68A, 68B. It is more preferable still that the plurality of fibers are stacked ten (10) times. As described above, the plurality of fibers 18 may include metal fibers, high tensile strength fibrous material, ceramic fibers, polymer fibers, elastomer fibers, or the like without departing from the scope of the present invention. As shown in FIG. 19, the support structure 17 may be disposed only partially within or on the elastomer layer generally along the longitudinal axis without departing from the scope of the present invention.

Referring again to FIGS. 9-13, the material of the present invention can be an all purpose material for use as desired by a person to regulate energy by distributing and partially dissipating energy exerted thereon. When the material 10 of the present is used as an all purpose material, the all purpose material 10 includes a material body 70 that is elongateable along the stretch axis 50 from a first position (shown in FIGS. 2, 9, and 12) to a second position (shown in FIGS. 11 and 13), in which the material body 70 is elongated by a predetermined amount relative to the first position. The stretch axis 50 is preferably determined during manufacturing by the orientation and geometry of the support structure 17 which preferably limits the directions in which the material body 70 can elongate. If multiple separate material bodies 70 are stacked together, it may be desirable to have the stretch axis 50 of the individual material bodies 70 oriented askew from each other.

The first elastomer layer 12 defines a material length 72, as measured along the stretch axis 50 of the material body 70. The support structure 17 is preferably disposed within the elastomer layer 12 generally along the stretch axis 50 in an at least partially non linear fashion while the material body 70 is in the first position so that a length of the support structure, as measured along the surface thereof, is greater than the material length 72 of the first elastomer layer. When the material body 70 is elongated into the second position, the support structure 17 is at least partially straightened so that the support structure is more linear, relative to when the material body 70 is in the first position.

The support structure 17 is preferably positioned in a sinusoidal fashion within any of the materials 10 of the present invention. The support structure 17 or ribbon may also be positioned in the form of a triangular wave, square wave, or an irregular fashion without departing from the scope of the present invention.

Any of the materials of the present invention may be formed with an elastomer layer 12 formed by silicone or any other suitable material. Depending upon the application, the vibration absorbing material 12 may be a thermoset and/or may be free of voids therein.

Any of the embodiments of the material 10 of FIGS. 1-33 can be used as an implement cover, grip, athletic tape, an all purpose material, a brace, and/or padding. When the material 10 of the present invention is used as part of a padding, the padding includes a padding body 74 that is elongateable along the stretch axis from a first position (shown in FIGS. 2, 9, and 12) to a second position (shown in FIGS. 11 and 13), in which the padding body 74 is elongated by a predetermined amount relative to the first position. The padding includes a first elastomer layer 12 which defines a padding length 76, as measured along the stretch axis 50 of the padding body 74.

The support structure 17 is disposed within the elastomer layer 12 generally along the stretch axis 50 in an at least partially non linear fashion while the padding body 74 is in the first position so that a length of the support structure 17, is measured along a surface thereof, is greater than the padding length 76 of the first elastomer layer 12. When the padding body 74 is elongated into the second position, the support structure 17 is at least partially straightened so that the support structure is more linear, relative to when the padding body 74 is in the first position. The straightening of the support structure 17 causes energy to be dissipated and generally prevents further elongation of the elastomer layer along the stretch axis 50 past the second position.

When the materials 10 of the present invention are incorporated as part of a brace, the brace provides a controlled support for a wrapped portion of a person's body. The brace includes a brace body 78 that is elongateable along the stretch axis 50 from a first position (shown in FIGS. 2, 9, and 12) to a second position (shown in FIGS. 11 and 13), in which the brace body 78 is elongated by a predetermined amount relative to the first position. The brace body includes a first elastomer layer 12 that defines a brace length 80, as measured along the stretch axis 50, of the brace body 78.

The support structure 17 is preferably disposed within the elastomer layer generally along the stretch axis 50 in an at least partially non linear fashion while the brace body 78 is in the first position so that a length of the support structure 17, as measured along a surface thereof, is greater than the brace length 80 of the first elastomer layer 12. When the brace body 78 is stretched into the second position, the support structure 17 is at least partially straightened so that the support structure 17 is more linear, relative to when the brace body 78 is in the first position. The straightening of the support structure 17 causes energy to be dissipated and preferably generally prevents further elongation of the elastomer layer 12 along the stretch axis past the second position. Those ordinarily skilled in the art will appreciate that any of the materials 10 of the present invention may be formed into a one piece brace that provides a controlled support as described above without departing from the scope of the present invention.

Referring to FIGS. 9 and 12, depending upon the geometry of the support structure 17 when the material 10 is in the first position, the amount of stretch of the material 10 can be selected. It is preferred that the percentage increase in the material length when the body 64, 70, 74, 78 moves from the first position to the second position is selected based on a desired range of motion. When the material 10 is configured as an athletic tape, the athletic tape may be wrapped about a portion of a person's body multiple times, if necessary, to form a brace. Alternatively, a single layer of material 10 can be wrapped on a person and secured in place using conventional athletic tape or the like. It is preferable that the successive wrappings of athletic tape are affixed to each other to form a generally one piece brace. This can be accomplished by using tape that is self fusing to allow multiple adjacent wrappings of the athletic tape to fuse together to form an integral piece. One method of fusing wrappings of the athletic tape is for the elastomer layer of each of the multiple adjacent wrappings to contact the elastomer layer of the adjacent wrappings to fuse together to form a single elastomer layer. Self fusing technology can be used with any of the materials 10 of the present invention and can be used in any of the applications for which those materials are suitable. By way of non limiting example, self fusing material 10 can be used with baseball bats, lacrosse sticks, tennis rackets, gun covers and wraps, implements, sports implements, tape, padding, braces, or the like.

Figure 14:
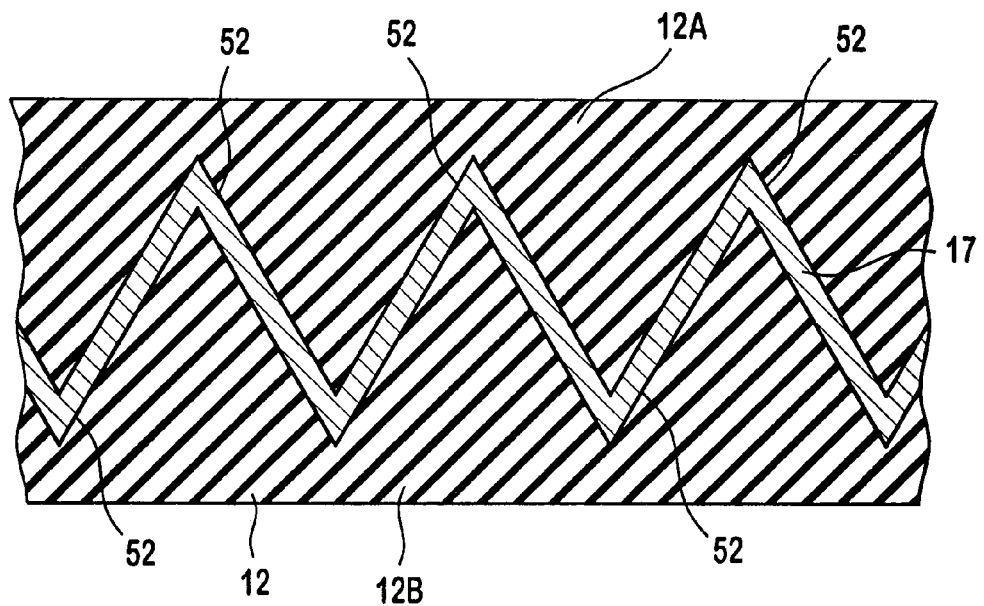
FIG. 14 is a cross-sectional view of a fourth preferred embodiment of the material of the present invention illustrating the support structure with an adhesive layer generally over its major surfaces to allow the elastomer material to be secured thereto rather than molded and/or extruded thereover.
Figure 15:
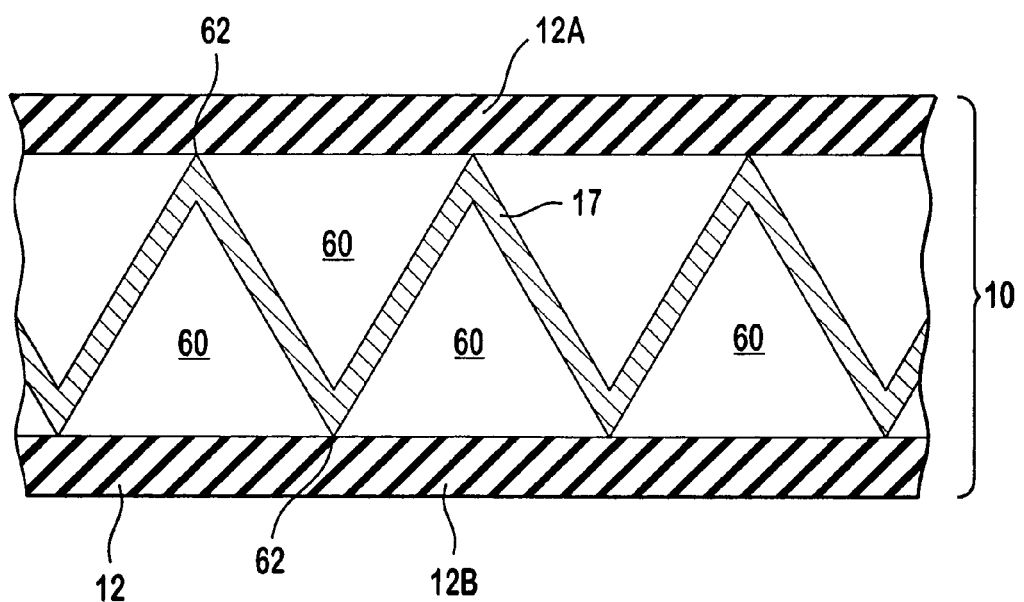
FIG. 15 is a cross-sectional view of a fifth preferred embodiment of the material of the present invention illustrating the support structure, or ribbon material, positioned between two spaced elastomer layers with the support structure's peaks molded, fastened, and/or otherwise affixed to the elastomer layer at a plurality of locations; air gaps are preferably present about the support structure to facilitate longitudinal stretching of the material; alternatively, the support structure can be secured only at its lateral ends (i.e., the left and right ends of the support structure viewed in FIG. 15) to the elastomer layers so that the remainder of the support structure moves freely within an outer sheath of elastomer material and functions as a spring/elastic member to limit the elongation of the material.
Figure 16:
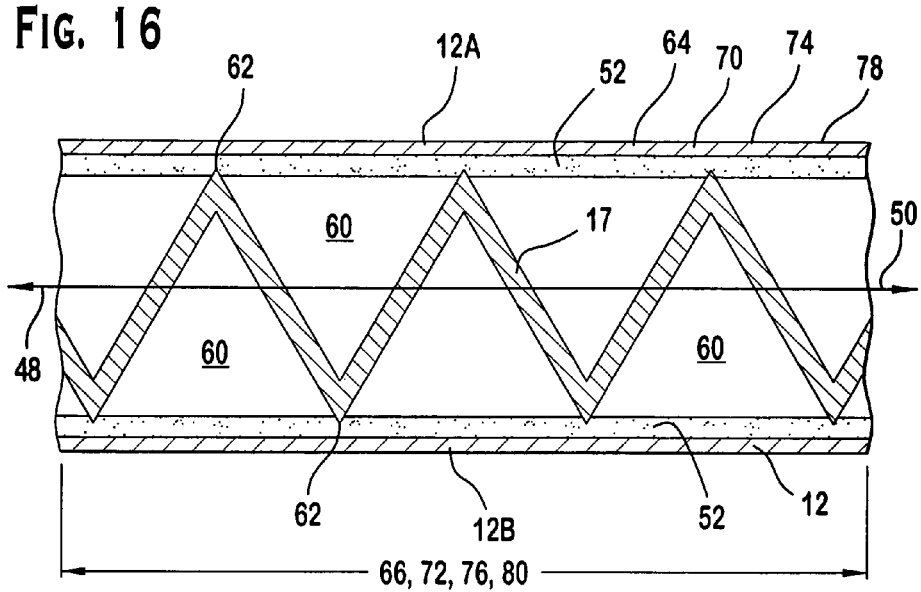
FIG. 16 is a sixth preferred embodiment of the vibration dissipating material of the present invention and is similar to the material shown in FIG. 15, except that the support structure's peaks are secured to the elastomer layers via an adhesive layer.
Figure 17:
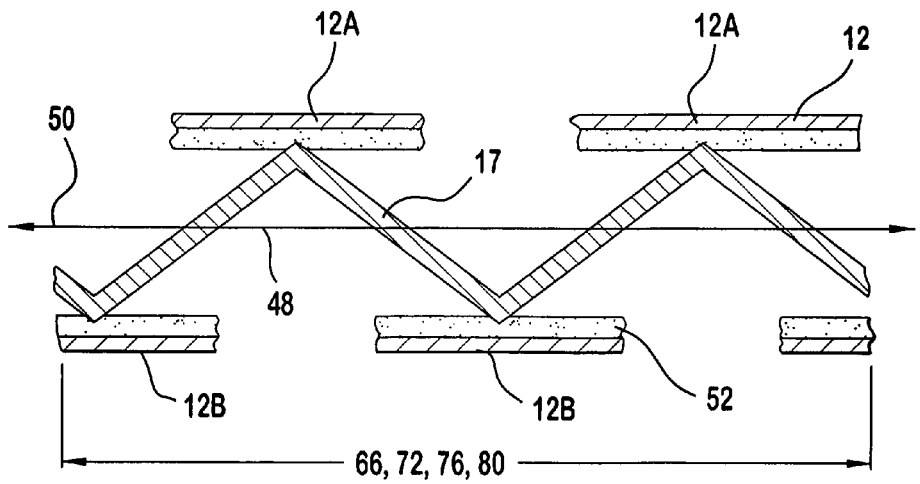
FIG. 17 is a seventh preferred embodiment of the vibration dissipating material of the present invention and illustrates the vibration dissipating material and any accompanying adhesive actually physically breaking when the support structure is elongated into the second position; the breaking of the vibration dissipating material results in further energy dissipation and vibration absorption in addition to that dissipated by the support structure.
Figure 18:
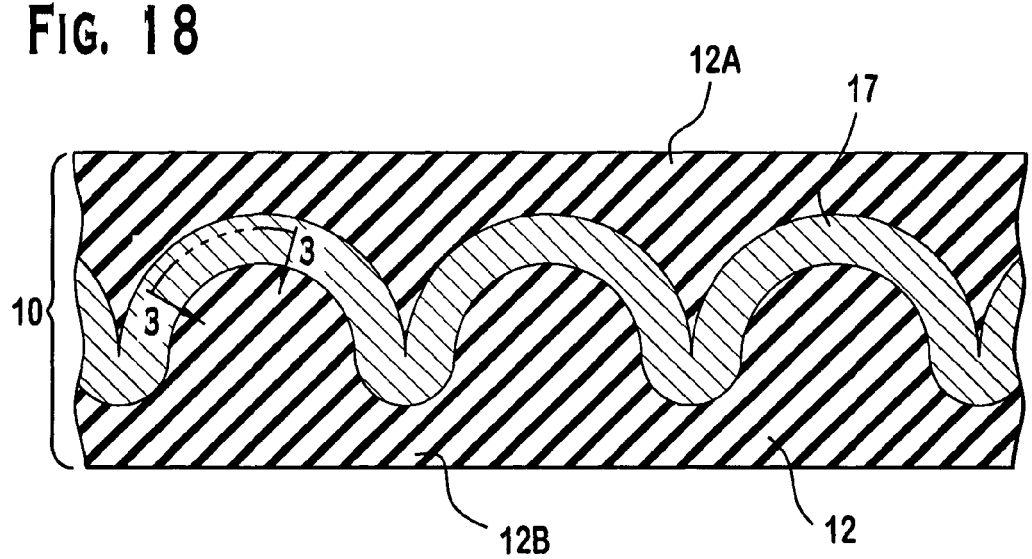
FIG. 18 is an eighth preferred embodiment of the vibration dissipating material of the present invention and illustrates that the support structure, or ribbon material, can be disposed in any geometry within the vibration dissipating material; additionally, individually rigid squares, buttons, or plates (not shown) can be positioned on one side of the material to further spread impact force along the surface of the material prior to the dissipation of vibration by the material in general; additionally, such buttons, plates, or other rigid surfaces can be attached directly to a mesh or other flexible layer that is disposed over the material shown in FIG. 18 so that impact force on one of the rigid members causes deflection of the entire mesh or other layer for energy absorption prior to vibration absorption by the material; the section line labeled 3-3 in this Figure signifies that it is possible that the support structure shown in FIG. 18 is generally the same as that illustrated in FIG. 3.

Referring to FIGS. 14, 16, and 17, adhesive 52 may be used to connect the support structure 17 to the vibration absorbing material 12. Referring to FIGS. 15-17, air gaps 60 can be present proximate to the support structure 17 without departing from the scope of the present invention. Referring to FIG. 15, the sixth preferred embodiment of the material of the present invention can be secured at its peak 62 to the vibrating absorbing material 12 or can be secured only at its ends with the vibration absorbing material 12 forming a protective sheath for the support structure 17 which would act as an elastic member in this instance.

Figure 22:
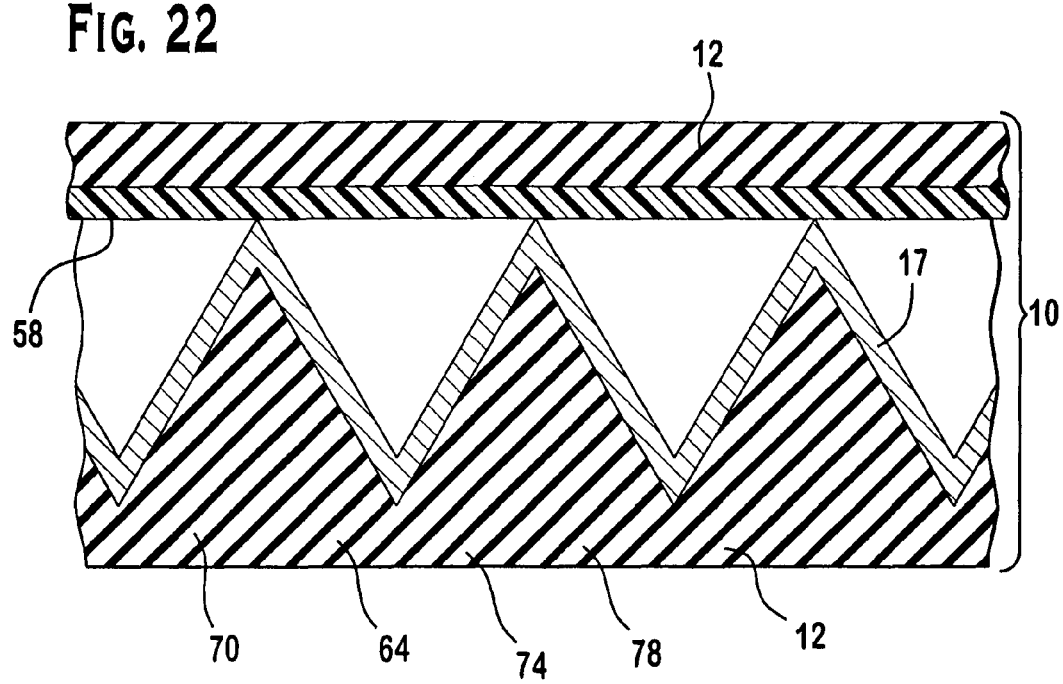
FIG. 22 is a twelfth preferred embodiment of the vibration absorbing material of the present invention and illustrates the shrinkable layer being disposed over peaks of the support structure with an optional vibration absorbing layer thereover.
Figure 23:
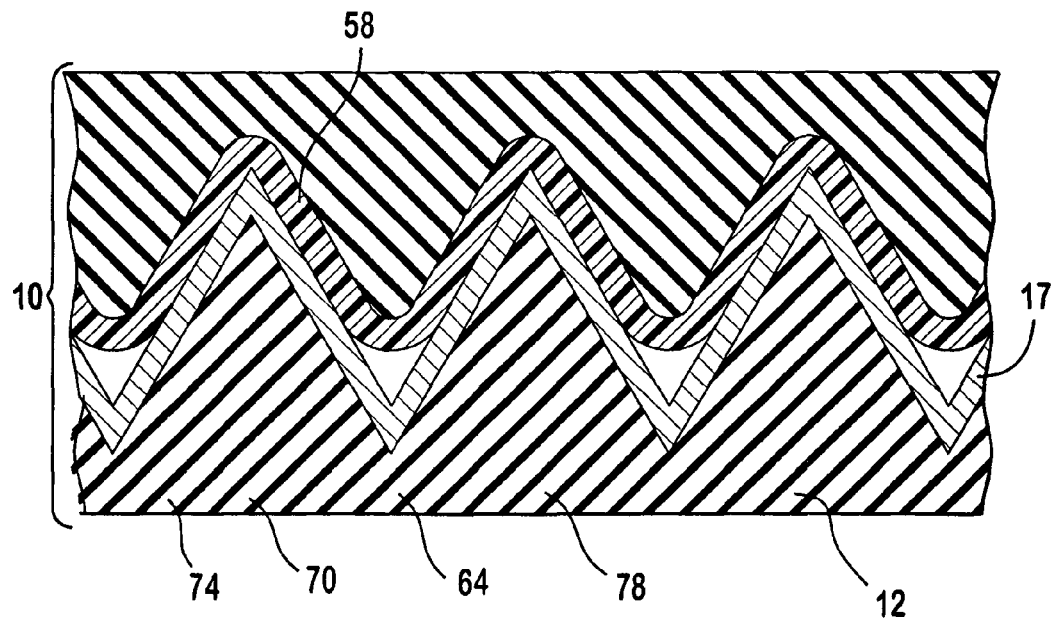
FIG. 23 is a cross-sectional view of the material of FIG. 22 when the shrinkable layer has been shrunk down over the support structure after the material is placed in a desired configuration; although the optional additional vibration absorbing material is not shown in FIG. 23, it can be left in position above the shrinkable layer to form a protective sheath or also pulled down into the gaps between the peaks of the support structure.
Figure 24:
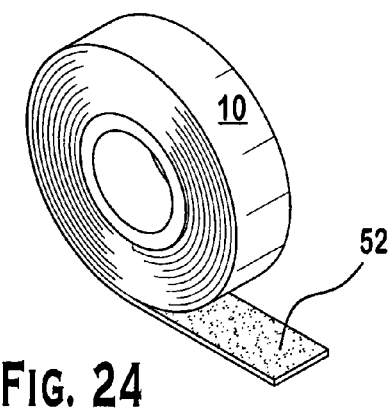
FIG. 24 illustrates the material of the present invention configured as athletic tape with an optional adhesive layer.
Figure 25:
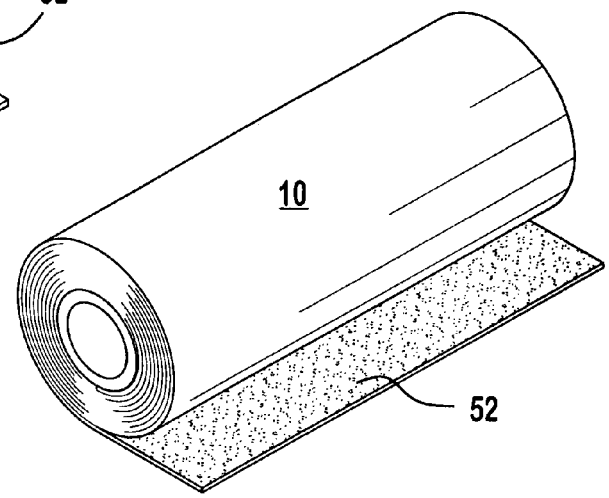
FIG. 25 illustrates the material of the present invention as a roll of material/padding/wide wrap material or the like with an optional adhesive layer thereon.
Figure 26:
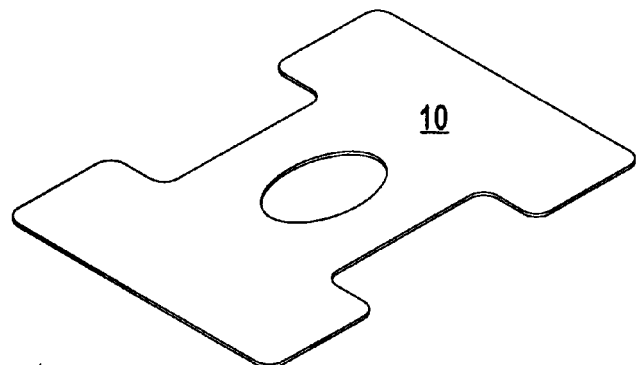
FIG. 26 illustrates the material of the present invention configured as a knee bandage.
Figure 27:
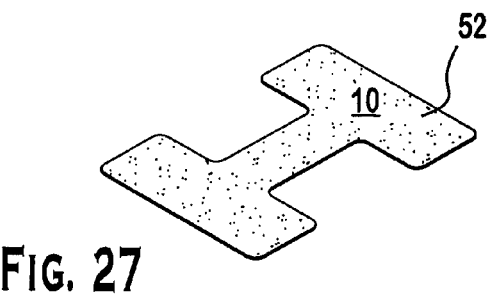
FIG. 27 illustrates the material of the present invention with an optional adhesive layer configured as a finger and/or joint bandage; while various bandages, wraps, padding, materials, tapes, or the like are shown, the material of the present invention can be used for any purpose or application without departing from the scope of the present invention.
Figure 28:
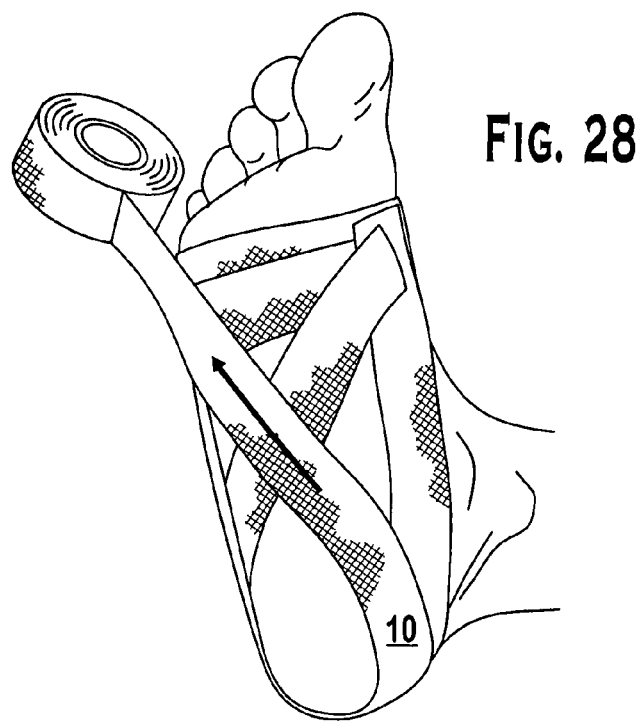
FIG. 28 illustrates the material of the present invention used to form a foot brace.
Figure 29:
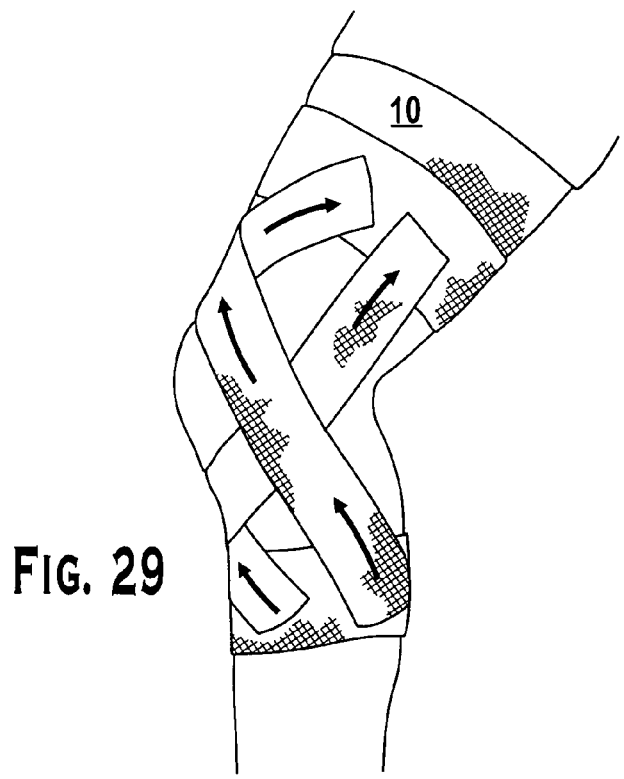
FIG. 29 illustrates the material of the present invention wrapped to form a knee supporting brace.
Figure 30:
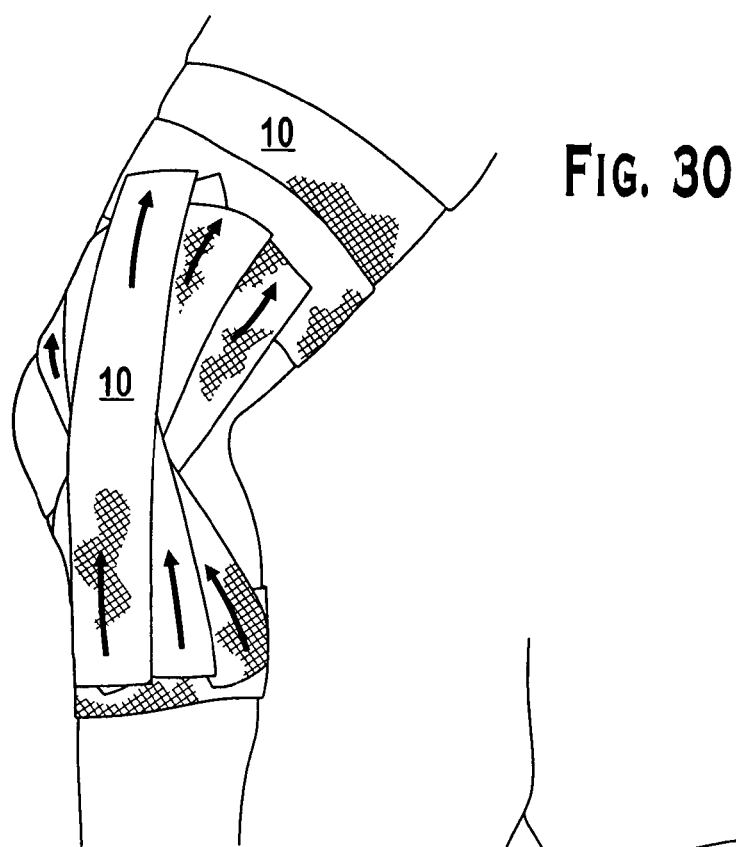
FIG. 30 illustrates additional layers of material used to brace the ligaments in a person's leg.
Figure 31:
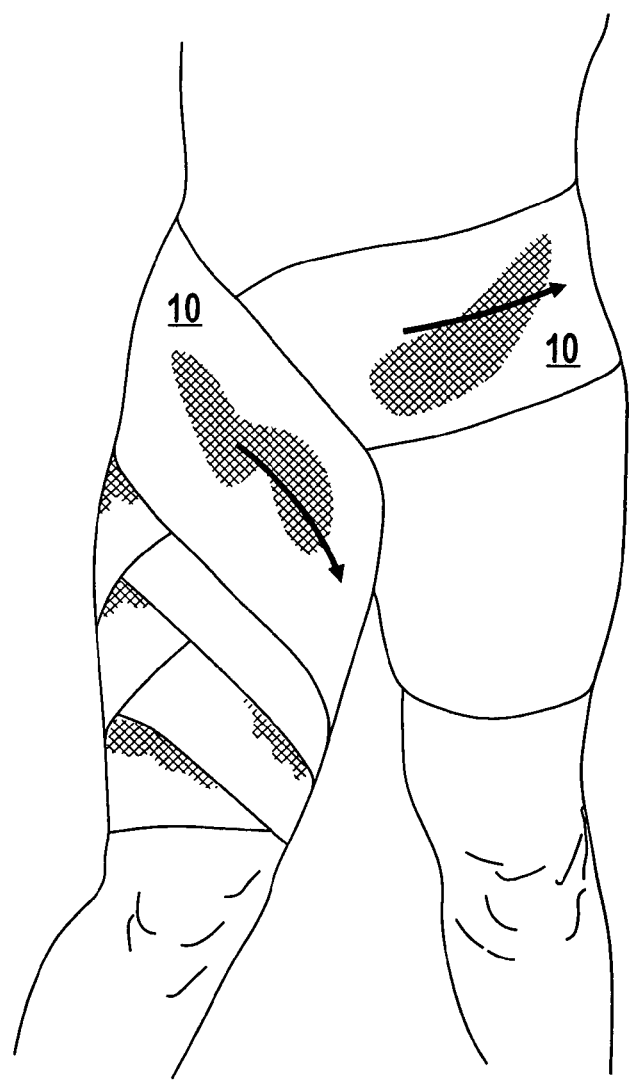
FIG. 31 illustrates the material of the present invention used to form a hip support.
Figure 32:
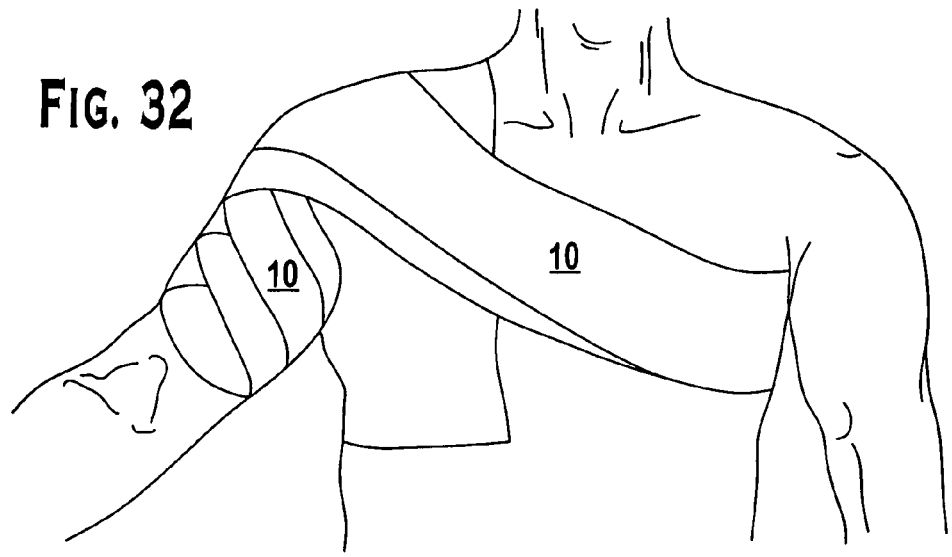
FIG. 32 illustrates the material of the present invention used to form a shoulder brace.
Figure 33:
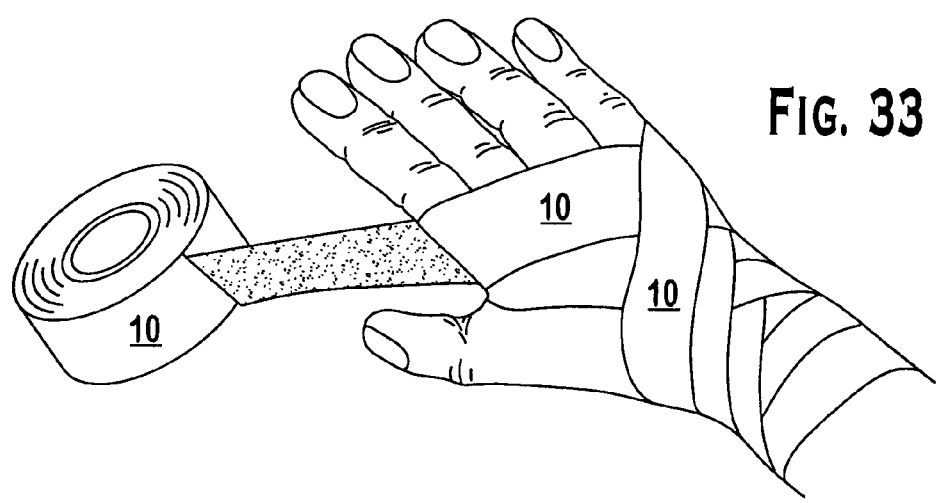
FIG. 33 illustrates the material of the present invention wrapped to form a hand and wrist brace; while the material of the present invention has been shown in conjunction with various portions of the person's body, those of ordinary skill in the art will appreciate from this disclosure that the material of the present invention can be used as an athletic brace, a medical support, or a padding for any portion of a person's body without the departing from the scope of the present invention.

FIGS. 20-23 illustrate the material 10 of the present invention incorporating a shrink layer 58 which can be used to secure the material 10 in position. Additionally, the shrinkable layer 58 may be configured to break when a certain stress threshold is reached to provide further energy dissipation. Referring to FIG. 22, a shrinkable layer 58 is in its pre-shrink configuration. Referring to FIG. 23, once the shrinkable layer 58 has been activated, the shrinkable layer 58 preferably deforms about one side of the support structure 17 to hold the material 10 in position. The shrinkable layer 58 can be heat or water activated. Alternative known activation methods are also suitable for use with the present invention.

FIG. 17 illustrates a seventh preferred embodiment of the present invention in which the vibration absorbing layer 12 is configured to break apart during the elongation of the support structure 17 to allow for greater energy dissipation.

Any of the materials 10 of the present invention can be used in conjunction with additional layers of rigid or flexible materials without departing from the scope of the present invention. For example, the materials 10 of the present invention may be used with a hard shell outer layer which is designed to dissipate impact energy over the entire material 10 prior to the material 10 deforming to dissipate energy. One type of rigid material that can be used in combination with the materials 10 of the present invention is molded foam. Molded foam layers preferably include multiple flex seams that allow portions of the foam layer to at least partially move relative to each other even though the overall foam layer is a single body of material. This is ideal for turning an impact force into a more general blunt force that is spread over a larger area of the material 10. Alternatively, individual foam pieces, buttons, rigid squares, or the like can be directly attached to an outer surface of any of the materials 10 of the present invention. Alternatively, such foam pieces, buttons, rigid squares, or the like can be attached to a flexible layer or fabric that will dissipate received impact energy over the length of the fabric fibers prior to the dissipation of energy by the material 10.

FIGS. 34-35 illustrate another embodiment of the present invention. As shown therein a cover in the form of a sleeve 210 is mounted on the handle or lower portion 218 of a baseball bat 210. Sleeve 210 is premolded so that it can be fit onto the handle portion of the bat 212 in a quick and convenient manner. This can be accomplished by having the sleeve 210 made of a stretchable or resilient material so that its upper end 214 would be pulled open and could be stretched to fit over the knob 217 of the bat 212. Alternatively, or in addition, sleeve 210 may be provided with a longitudinal slit 16 to permit the sleeve to be pulled at least partially open and thereby facilitate snapping the sleeve 210 over the handle 218 of the bat 212. The sleeve would remain mounted in place due to the tacky nature of the sleeve material and/or by the application of a suitable adhesive on the inner surface of the sleeve and/or on the outer surface of handle 218.

A characterizing feature of sleeve 210, as illustrated in FIGS. 34-35, is that the lower end of the sleeve includes an outwardly extending peripheral knob 220. Knob 220 could be a separate cap snapped onto or secured in any other manner to the main portion of sleeve 210. Alternatively, knob 220 could be integral with and molded as part of the sleeve 210.

In a broad practice of this invention, sleeve 210 can be a single layer. The material would have the appropriate hardness and vibration dampening characteristics. The outer surface of the material would be tacky having high friction characteristics.

Alternatively, the sleeve 210 could be formed from a two layer laminate where the vibration absorbing material forms the inner layer disposed against the handle, with a separate tacky outer layer made from any suitable high friction material such as a thermoplastic material with polyurethane being one example. Thus, the two layer laminate would have an inner elastomer layer which is characterized by its vibration dampening ability, while the main characteristic of the outer elastomer layer is its tackiness to provide a suitable gripping surface that would resist the tendency for the user's hand to slide off the handle. The provision of the knob 220 also functions both as a stop member to minimize the tendency for the handle to slip from the user's hand and to cooperate in the vibration dampening affect.

FIG. 35 illustrates the preferred form of multilayer laminate which includes the inner vibration absorbing layer 222 and the outer tacky gripping layer 224 with an intermediate layer 226 made of a stiffening material which dissipates force. If desired layer 226 could be innermost and layer 224 could be the intermediate layer. A preferred stiffening material would be aramid fibers which could be incorporated in the material in any suitable manner as later described with respect to FIGS. 44-47. However, fiberglass or any high tensile strength fibrous material can be used as the stiffening material forming the layer. Additionally, in one embodiment, the stiffening layer is substantially embedded in or held in place by the elastomer layer(s).

FIG. 36 schematically shows what is believed to be the affect of the shock forces from vibration when the implement makes contact such as from the bat 212 striking a ball. FIG. 36 shows the force vectors in accordance with a three layer laminate, such as illustrated in FIG. 35, wherein elastomeric layers 222, 224 are made of a silicone material. The intermediate layer 226 is an aramid layer made of aramid fibers. The initial shock or vibration is shown by the lateral or transverse arrows 228 on each side of the sleeve laminate 210. This causes the elastomeric layers 222, 224 to be compressed along the arc 230. The inclusion of the intermediate layer 226 made from a force dissipating material spreads the vibration longitudinally as shown by the arrows 232. The linear spread of the vibration causes a rebound effect which totally dampens the vibration.

Laboratory tests were carried out at a prominent university to evaluate various grips mounted on baseball bats. In the testing, baseball bats with various grips were suspended from the ceiling by a thin thread; this achieves almost a free boundary condition that is needed to determine the true characteristics of the bats. Two standard industrial accelerometers were mounted on a specially fabricated sleeve roughly in positions where the left hand and the right hand would grip the bat. A known force was delivered to the bat with a standard calibrated impact hammer at three positions, one corresponding to the sweet spot, the other two simulating "miss hits" located on the mid-point and shaft of the bat. The time history of the force as well as the accelerations were routed through a signal conditioning device and were connected to a data acquisition device. This was connected to a computer which was used to log the data.

Two series of tests were conducted. In the first test, a control bat (with a standard rubber grip, WORTH Bat-model #C405) was compared to identical bats with several "Sting-Free" grips representing practices of the invention. These "Sting-Free" grips were comprised of two layers of pure silicone with various types of high tensile fibrous material inserted between the two layers of silicone. The types of KEVLAR, a type of aramid fiber that has high tensile strength, used in this test were referenced as follows: "005", "645", "120", "909". Also, a bat with just a thick layer of silicone but no KEVLAR was tested. With the exception of the thick silicone (which was deemed impractical because of the excessive thickness), the "645" bat showed the best reduction in vibration magnitudes.

The second series of tests were conducted using EASTON Bats (model #BK8) with the "645" KEVLAR in different combinations with silicone layers: The first bat tested was comprised of one bottom layer of silicone with a middle layer of the "645" KEVLAR and one top layer of silicone referred to as "111". The second bat test was comprised of two bottom layers of silicone with a middle layer of KEVLAR and one top layer of silicone referred to as "211". The third bat tested was comprised of one bottom layer of silicone with a middle layer of KEVLAR and two top layers of silicone referred to as "112". The "645" bat with the "111" configuration showed the best reduction in vibration magnitudes.

In order to quantify the effect of this vibration reduction, two criteria were defined: (I) the time it takes for the vibration to dissipate to an imperceptible value; and, (2) the magnitude of vibration in the range of frequencies at which the human hand is most sensitive.

The sting-free grips reduced the vibration in the baseball bats by both quantitative measures. In particular, the "645" KEVLAR in a "111" configuration was the best in vibration reduction. In the case of a baseball bat, the "645" reduced the bat's vibration in about ⅕ the time it took the control rubber grip to do so. The reduction in peak magnitude of vibration ranged from 60% to 80%, depending on the impact location and magnitude.

It was concluded that the "645" KEVLAR grip in a "111" combination reduces the magnitude of sensible vibration by 80% that is induced in a baseball bat when a player hits a ball with it. This was found to be true for a variety of impacts at different locations along the length of the bat. Hence, a person using the "Sting-Free" grips of the invention would clearly experience a considerable reduction in the sting effect (pain) when using the "Sting-free" grip than one would with a standard grip.

In view of the above tests a particularly preferred practice of the invention involves a multilayer laminate having an aramid such as KEVLAR, sandwiched between layers of pure silicone. The above indicated tests show dramatic results with this embodiment of the invention. As also indicated above, however, the laminate could comprise other combinations of layers such as a plurality of bottom layers of silicone or a plurality of top layers of silicone other variations include a repetitive laminate assembly wherein a vibration dampening layer is innermost with a force dissipating layer against the lower vibration dampening layer and then with a second vibration dampening layer over the force dissipating layer followed by a second force dissipating layer, etc. with the final laminate layer being a gripping layer which could also be made of vibration dampening material. Among the considerations in determining which laminate should be used would be the thickness limitations and the desired vibration dampening properties.

The various layers could have different relative thicknesses. Preferably, the vibration dampening layer, such as layer 222, would be the thickest of the layers. The outermost gripping layer, however, could be of the same thickness as the vibration dampening layer, such as layer 224 shown in FIG. 35 or could be a thinner layer since the main function of the outer layer is to provide sufficient friction to assure a firm gripping action. A particularly advantageous feature of the invention where a force dissipating stiffening layer is used is that the force dissipating layer could be very thin and still achieve its intended results. Thus, the force dissipating layer would preferably be the thinnest of the layers, although it might be of generally the same thickness as the outer gripping layer. If desired the laminate could also include a plurality of vibration dampening layers (such as thin layers of gel material) and/or a plurality of stiffening force dissipating layers. Where such plural layers are used, the various layers could differ in the thickness from each other.

FIGS. 34-35 show the use of the invention where the sleeve 210 is mounted over a baseball bat 212 having a knob 217. The same general type structure could also be used where the implement does not have a knob similar to a baseball bat knob. FIG. 37, for example, illustrates a variation of the invention wherein the sleeve 210A would be mounted on the handle 218A of an implement that does not terminate in any knob. Such implement could be various types of athletic equipment, tools, etc. The sleeve 210A, however, would still have a knob 2220A which would include an outer gripping layer 224A, an intermediate force dissipating layer 226A and an inner vibration dampening layer 222A. In the embodiment shown in FIG. 37, the handle 218A extends into the knob 220A. Thus, the inner layer 222A would have an accommodating recess 34 for receiving the handle 218A. The inner layer 222A would also be of greater thickness in the knob area as illustrated.

Figure 38:
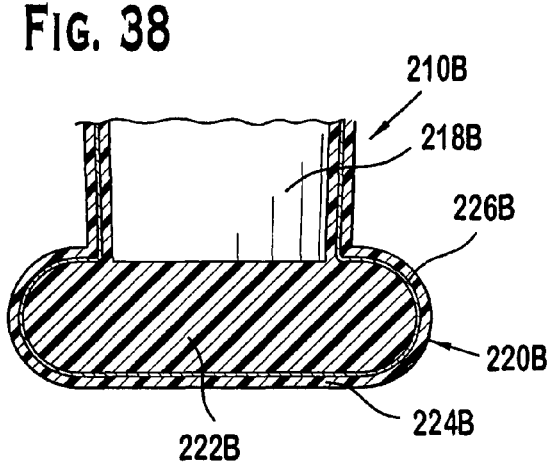
FIG. 38 is a view similar to FIGS. 35 and 39 showing still yet another form of sleeve in accordance with this invention.

FIG. 38 shows a variation where the sleeve 210B fits over handle 218B without the handle 218B penetrating the knob 220B. As illustrated, the outer gripping layer 224B would be of uniform thickness both in the gripping area and in the knob. Similarly, the intermediate force dissipating layer 226B would also be of uniform thickness. The inner shock absorbing layer 222B, however, would completely occupy the portion of the knob inwardly of the force dissipating layer 226B since the handle 218B terminates short of the knob 2220B.

Figure 39:
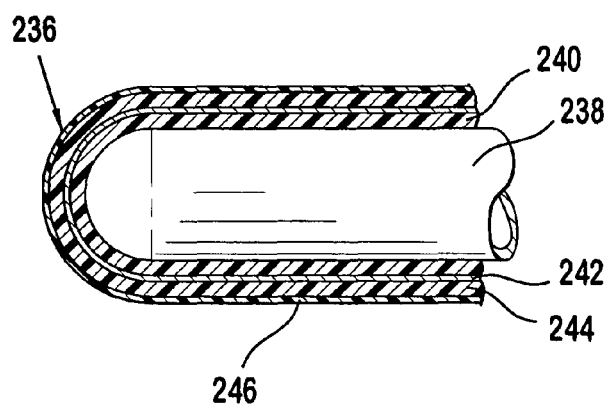
FIG. 39 is a cross-sectional longitudinal view showing an alternative cover in accordance with this invention mounted on a further type of implement.
Figure 41:
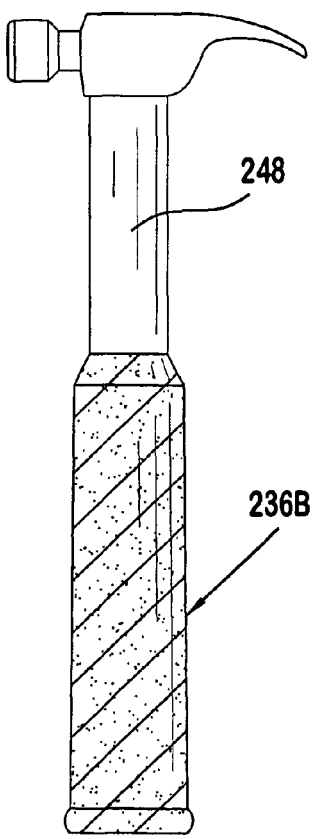
FIG. 41 is an elevational view of a hammer incorporating an abrasive dampening handle in accordance with this invention.

FIG. 39 shows a variation of the invention where the gripping cover 236 does not include a knob. As shown therein, the gripping cover would be mounted over the gripping area of a handle 238 in any suitable manner and would be held in place either by a previously applied adhesive or due to the tacky nature of the innermost vibration dampening layer 240 or due to resilient characteristics of the cover 236. Additionally, the cover might be formed directly on the handle 238. FIG. 41, for example, shows a cover 236B which is applied in the form of tape.

As shown in FIG. 39 the cover 236 includes one of the laminate variations where a force dissipating layer 242 is provided over the inner vibration dampening layer 240 with a second vibration dampening layer 244 applied over force dissipating layer 242 and with a final thin gripping layer 246 as the outermost layer. As illustrated, the two vibration dampening layers 240 and 244 are the thickest layers and may be of the same or differing thickness from each other. The force dissipating layer 242 and outer gripping layer 244 are significantly thinner.

Figure 40:
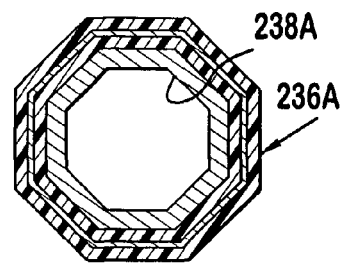
FIG. 40 is a cross-sectional end view of yet another cover in accordance with this invention.

FIG. 40 shows a cover 236A mounted over a hollow handle 238A which is of non-circular cross-section. Handle 238A may, for example, have the octagonal shape of a tennis racquet.

FIG. 41 shows a further cover 236B mounted over the handle portion of tool such as hammer 248. As illustrated, the cover 236B is applied in tape form and would conform to the shape of the handle portion of hammer 248. Other forms of covers could also be applied rather than using a tape. Similarly, the tape could be used as a means for applying a cover to other types of implements.

Figure 42:
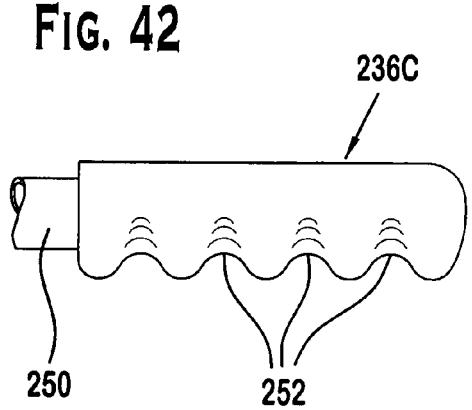
FIG. 42 is an elevational view showing a portion of a handlebar incorporating a vibration dampening cover in accordance with this invention.

FIG. 42 illustrates a cover 236C mounted over the end of a handlebar, such as the handlebar of various types of cycles or any other device having a handlebar including steering wheels for vehicles and the like. FIG. 42 also illustrates a variation where the cover 236C has an outer contour with finger receiving recesses 252. Such recesses could also be utilized for covers of other types of implements.

Figure 43:
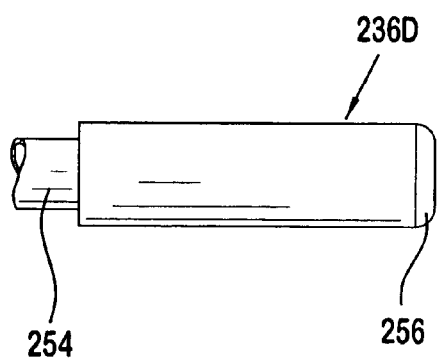
FIG. 43 is a view similar to FIG. 42 of yet another practice of this invention.

FIG. 43 illustrates a variation of the invention where the cover 236D is mounted to the handle portion of an implement 254 with the extreme end 256 of the implement being bare. This illustration is to show that the invention is intended to provide a vibration dampening gripping cover for the handle of an implement and that the cover need not extend beyond the gripping area. Thus, there could be portions of the implement on both ends of the handle without having the cover applied to those portions.

In a preferred practice of the invention, as previously discussed, a force dissipating stiffening layer is provided as an intermediate layer of a multilayer laminate where there is at least one inner layer of vibration dampening material and an outer layer of gripping material with the possibility of additional layers of vibration dampening material and force dissipating layers of various thickness. As noted the force dissipating layer could be innermost. The invention may also be practiced where the laminate includes one or more layers in addition to the gripping layer and the stiffening layer and the vibration dampening layer. Such additional layer(s) could be incorporated at any location in the laminate, depending on its intended function (e.g., an adhesive layer, a cushioning layer, etc.).

Figure 44:
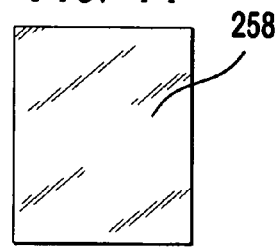
FIGS. 44-47 are plan views of various forms of the intermediate force dissipating layer which is used in certain practices of this invention.
Figure 45:
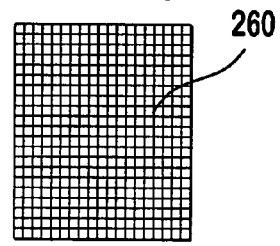
Figure 46:
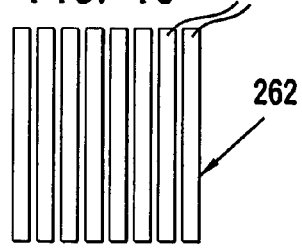
Figure 47:
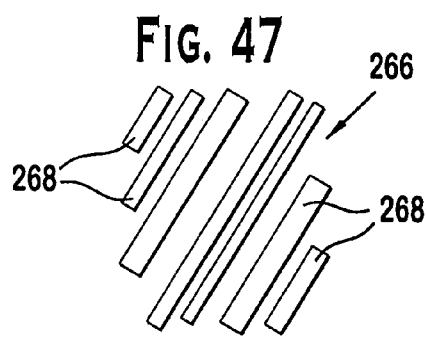

The force dissipating layer could be incorporated in the laminate in various manners. FIG. 44, for example, illustrates a force dissipating stiffening layer 258 in the form of a generally imperforate sheet. FIG. 45 illustrates a force dissipating layer 260 in the form of an open mesh sheet. This is a particularly advantageous manner of forming the force dissipating layer where it is made of KEVLAR fibers. FIG. 46 illustrates a variation where the force dissipating layer 262 is formed from a plurality of individual strips of material 264 which are parallel to each other and generally identical to each other in length and thickness as well as spacing. FIG. 47 shows a variation where the force dissipating layer 266 is made of individual strips 268 of different sizes and which could be disposed in a more random fashion regarding their orientation. Although all of the strips 268 are illustrated in FIG. 47 as being parallel, non-parallel arrangements could also be used.

The vibration dampening grip cover of this invention could be used for a wide number of implements. Examples of such implements include athletic equipment, hand tools and handlebars. For example, such athletic equipment includes bats, racquets, sticks, javelins, etc. Examples of tools include hammers, screwdrivers, shovels, rakes, brooms, wrenches, pliers, knives, handguns, air hammers, etc. Examples of handlebars include motorcycles, bicycles and various types of steering wheels.

A preferred practice of this invention is to incorporate a force dissipating layer, particularly an aramid, such as KEVLAR fiber, into a composite with at least two elastomers. One elastomer layer would function as a vibration dampening material and the other outer elastomer layer which would function as a gripping layer. The outer elastomer layer could also be a vibration dampening material. Preferably, the outer layer completely covers the composite.

There are an almost infinite number of possible uses for the composite of laminate of this invention. In accordance with the various uses the elastomer layers may have different degrees of hardness, coefficient of friction and dampening of vibration. Similarly, the thicknesses of the various layers could also vary in accordance with the intended use. Examples of ranges of hardness for the inner vibration dampening layer and the outer gripping layer (which may also be a vibration absorbing layer) are 5-70 Durometer Shore A. One of the layers may have a range of 5-20 Durometer Shore A and the other a range of 30-70 Durometer Shore A for either of these layers. The vibration dampening layer could have a hardness of less than 5, and could even be a 000 Durometer reading. The vibration dampening material could be a gel, such as a silicone gel or a gel of any other suitable material. The coefficient of friction as determined by conventional measuring techniques for the tacky and non-porus gripping layer is preferably at least 0.5 and may be in the range of 0.6-1.5. A more preferred range is 0.7-1.2 with a still more preferred range being about 0.8-1. The outer gripping layer, when also used as a vibration dampening layer, could have the same thickness as the inner layer. When used solely as a gripping layer the thickness could be generally the same as the intermediate layer, which might be about ¹⁄₂₀ to ¼ of the thickness of the vibration dampening layer.

The grip cover of this invention could be used with various implements as discussed above. Thus, the handle portion of the implement could be of cylindrical shape with a uniform diameter and smooth outer surface such as the golf club handle 238 shown in FIG. 37. Alternatively, the handle could taper such as the bat handle shown in FIGS. 34-35. Other illustrated geometric shapes include the octagonal tennis racquet handle 238A shown in FIG. 40 or a generally oval type handle such as the hammer 248 shown in FIG. 41. The invention is not limited to any particular geometric shape. In addition, the implement could have an irregular shape such as a handle bar with finger receiving depressions as shown in FIG. 42. Where the outer surface of the implement handle is of non-smooth configuration the inner layer of the cover could press against and generally conform to the outer surface of the handle and the outermost gripping layer of the cover could include its own finger receiving depressions. Alternatively, the cover may be of uniform thickness of a shape conforming to the irregularities in the outer surface of the handle.

It is recognized by those skilled in the art, that changes may be made to the above-described embodiments of the invention without departing from the broad inventive concept thereof. For example, the material 10 may include additional layers (e.g., two or more additional layers) without departing from the scope of the present invention. It is understood, therefore, that this invention is not limited to the particular embodiments disclosed, but is intended to cover all modifications which are within the spirit and scope of the invention as defined by the appended claims and/or shown in the attached drawings.

We claim:

1. An athletic tape for wrapping a portion of a person's body, the athletic tape having a longitudinal axis and being adapted to provide a controlled support for the portion of the person's body, the athletic tape comprising:

a tape body being stretchable along the longitudinal axis from a first position to a second position, in which the tape body is elongated by a predetermined amount relative to the first position, the tape body comprising:

a first elastomer layer defining a tape length, as measured along the longitudinal axis, of the tape body;

a support structure comprising a plurality of interconnected fibers which define a continuous planar structure disposed within the elastomer layer generally along the longitudinal axis in an at least partially non linear fashion while the tape body is in the first position so that a length of the support structure, as measured along a surface thereof, is greater than the tape length of the first elastomer layer; and wherein when the tape body is stretched into the second position, the support structure is at least partially straightened so that the support structure is more linear, relative to when the tape body is in the first position, the straightening of the support structure causing energy to be dissipated and generally preventing further elongation of the elastomer layer along the longitudinal axis past the second position.

2. The athletic tape of claim 1, wherein the plurality of fibers include high tensile fibrous material.

3. The athletic tape of claim 2, wherein the plurality of fibers are woven into a ribbon.

4. The athletic tape of claim 3, wherein the ribbon is positioned in a generally sinusoidal fashion within the elastomer layer while the tape body is in the first position.

5. The athletic tape of claim 2, wherein the plurality of fibers are woven.

6. The athletic tape of claim 1, wherein the tape body has top and bottom surfaces, the bottom surface facing the portion of the person's body when the athletic tape is wrapped thereover, the plurality of fibers defining multiple, stacked fiber layers between the top and bottom surfaces.

7. The athletic tape of claim 6, wherein the plurality of fibers are stacked between four (4) and sixteen (16) times between the top and bottom surfaces.

8. The athletic tape of claim 7, wherein the plurality of fibers are stacked ten (10) times.

9. The athletic tape of claim 1, wherein the athletic tape is wrapped around the portion of the person's body at least twice to form a brace.

10. The athletic tape of claim 9, wherein successive wrappings of the athletic tape are affixed to each other to form a generally one piece brace.

11. The athletic tape of claim 1, wherein the athletic tape is self fusing to allow multiple adjacent wrappings of the athletic tape to fuse together to form an integral piece.

12. The athletic tape of claim 11, wherein the elastomer layer of each of the multiple adjacent wrappings contacts the elastomer layer of the adjacent wrappings to fuse together to form a single elastomer layer.

13. The athletic tape of claim 11, wherein the integral piece is waterproof.

14. The athletic tape of claim 12, wherein the elastomer layer comprises silicone.

15. The athletic tape of claim 1, wherein the plurality of fibers include fiberglass fibers.

16. The athletic tape of claim 1, wherein the plurality of fibers include metal fibers.

17. The athletic tape of claim 1, wherein the plurality of fibers include ceramic fibers.

18. The athletic tape of claim 1, wherein the percentage increase in the tape length when the tape body moves from the first position to the second position is selected based on a desired range of motion for the portion of the person's body.

19. An athletic tape for wrapping a portion of a person's body, the athletic tape having a longitudinal axis and being adapted to provide a controlled support for the portion of the person's body, the athletic tape comprising:
  a tape body being stretchable along the longitudinal axis from a first position to a second position, in which the tape body is elongated by a predetermined amount relative to the first position, the tape body comprising:
    a first elastomer layer defining a tape length, as measured along the longitudinal axis, of the tape body;
    a support structure comprising a plurality of interconnected fibers which define a continuous planar structure disposed at least partially within the elastomer layer generally along the longitudinal axis in an at least partially non linear fashion while the tape body is in the first position so that a length of the support structure, as measured along a surface thereof, is greater than the tape length of the first elastomer layer; and
  wherein when the tape body is stretched into the second position, the support structure is at least partially straightened so that the support structure is more linear, relative to when the tape body is in the first position, the straightening of the support structure causing energy to be dissipated and generally preventing further elongation of the elastomer layer along the longitudinal axis past the second position.

20. The athletic tape of claim 19, wherein the support structure comprises a plurality of cloth layers.

21. The athletic tape of claim 20, wherein at least one of the plurality of cloth layers is formed of high tensile fibrous material.

22. The athletic tape of claim 19, wherein the support structure includes a first plurality of particles therein.

23. The athletic tape of claim 22, wherein the first elastomer layer includes a second plurality of particles.

24. The athletic tape of claim 23, wherein at least one of the first and second plurality of particles includes gel particles.

25. The athletic tape of claim 23, wherein at least one of the first and second plurality of particles includes sand particles.

26. The athletic tape of claim 23, wherein at least one of the first and second plurality of particles includes glass beads.

27. The athletic tape of claim 23, wherein at least one of the first and second plurality of particles includes chopped fibers.

28. The athletic tape of claim 23, wherein at least one of the first and second plurality of particles includes metal particles.

29. The athletic tape of claim 23, wherein at least one of the first and second plurality of particles includes foam particles.

30. The athletic tape of claim 19, wherein the support structure comprises a cloth layer.

31. The athletic tape of claim 19, wherein the support structure comprises a second elastomer having a plurality of particles therein.

32. A material having a stretch axis and being adapted to regulate energy by distributing and partially dissipating energy exerted thereon, the material comprising:
  a material body being elongateable along the stretch axis from a first position to a second position, in which the material body is elongated by a predetermined amount relative to the first position, the material body comprising:
    a first elastomer layer defining a material length, as measured along the stretch axis, of the material body;
    a support structure comprising a plurality of interconnected fibers which define a continuous planar structure disposed within the elastomer layer generally along the stretch axis in an at least partially non linear fashion while the material body is in the first position so that a length of the support structure, as measured along a surface thereof, is greater than the material length of the first elastomer layer; and
  wherein when the material body is elongated into the second position, the support structure is at least partially straightened so that the support structure is more linear, relative to when the material body is in the first position, the straightening of the support structure causing energy to be dissipated and generally preventing further elongation of the elastomer layer along the stretch axis past the second position.

33. The material of claim 32, wherein the support structure includes a first plurality of particles therein.

34. The material of claim 33, wherein the first elastomer layer includes a second plurality of particles.

35. The material of claim 34, wherein at least one of the first and second plurality of particles includes gel particles.

36. The material of claim 32, wherein the support structure is positioned in a generally sinusoidal fashion within the elastomer layer while the material body is in the first position.

37. The material of claim 36, wherein the elastomer layer comprises silicone.

38. The material of claim 32, wherein the support structure comprises a cloth layer.

39. The material of claim 32, wherein the support structure comprises a plurality of cloth layers.

40. The material of claim 32, wherein the support structure is generally positioned as at least one of a triangular wave and a square wave within the elastomer layer while the material body is in the first position.

41. The material of claim 32, further comprising a layer of shrinkable material.

42. The material of claim 41, wherein the shrinkable material is heat shrinkable.

43. The material of claim 41, wherein the shrinkable material is water shrinkable.

44. A padding for covering a portion of a person's body to provide support and/or impact force dissipation for the portion, the padding having a stretch axis, the padding comprising:
a padding body being elongateable along the stretch axis from a first position to a second position, in which the padding body is elongated by a predetermined amount relative to the first position, the padding body comprising:
a first elastomer layer defining a padding length, as measured along the stretch axis, of the padding body;
a support structure comprising a plurality of interconnected fibers which define a continuous planar structure disposed within the elastomer layer generally along the stretch axis in an at least partially non linear fashion while the padding body is in the first position so that a length of the support structure, as measured along a surface thereof, is greater than the padding length of the first elastomer layer; and
wherein when the padding body is elongated into the second position, the support structure is at least partially straightened so that the support structure is more linear, relative to when the padding body is in the first position, the straightening of the support structure causing energy to be dissipated and generally preventing further elongation of the elastomer layer along the stretch axis past the second position.

45. The padding of claim 44, further comprising a rigid layer of material disposed on at least part of the elastomer layer.

46. A brace for wrapping a portion of a person's body, the brace having a stretch axis and being adapted to provide a controlled support for the portion of the person's body, the brace comprising:
a brace body being elongateable along the stretch axis from a first position to a second position, in which the brace body is elongated by a predetermined amount relative to the first position, the brace body comprising:
a first elastomer layer defining a brace length, as measured along the stretch axis, of the brace body;
a support structure comprising a plurality of interconnected fibers which define a continuous planar structure disposed within the elastomer layer generally along the stretch axis in an at least partially non linear fashion while the brace body is in the first position so that a length of the support structure, as measured along a surface thereof, is greater than the brace length of the first elastomer layer; and
wherein when the brace body is stretched into the second position, the support structure is at least partially straightened so that the support structure is more linear, relative to when the brace body is in the first position, the straightening of the support structure causing energy to be dissipated and generally preventing further elongation of the elastomer layer along the stretch axis past the second position.

47. The brace of claim 46, wherein the brace is a one piece brace.

48. The brace of claim 46, wherein the brace comprises of multiple tape windings.

49. An athletic tape for wrapping a portion of a person's body, the athletic tape having a longitudinal axis and being adapted to provide a controlled support for the portion of the person's body, the athletic tape comprising:
a tape body being stretchable along the longitudinal axis from a first position to a second position, in which the tape body is elongated by a predetermined amount relative to the first position, the tape body comprising:
a first elastomer layer defining a tape length, as measured along the longitudinal axis, of the tape body;
a support structure comprising a plurality of interconnected fibers which define a continuous planar structure disposed over the elastomer layer and contacting the elastomer layer at a plurality of locations, the support structure extending generally along the longitudinal axis in an at least partially non linear fashion while the tape body is in the first position so that a length of the support structure, as measured along a surface thereof, is greater than the tape length of the first elastomer layer; and
wherein when the tape body is stretched into the second position, the support structure is at least partially straightened so that the support structure is more linear, relative to when the tape body is in the first position.

50. The athletic tape of claim 49, wherein the straightening of the support structure causes energy to be dissipated and generally prevents further elongation of the elastomer layer along the longitudinal axis past the second position.

51. The athletic tape of claim 49, further comprising a layer of shrinkable material.

52. The athletic tape of claim 51, wherein the shrinkable material is heat shrinkable.

53. The athletic tape of claim 51, wherein the shrinkable material is water shrinkable.

54. A material having a stretch axis and being adapted to regulate energy by distributing and partially dissipating energy exerted thereon, the material comprising:
a material body having first and second major surfaces and being elongateable along a stretch axis parallel to the major surface from a first position to a second position, in which the material body is elongated by a predetermined amount relative to the first position, the material body comprising:
a first elastomer layer defining a material length, as measured along the stretch axis, of the material body;
a support structure comprising a plurality of interconnected fibers which define a continuous planar structure disposed at least partially within the elastomer layer such that in the first position the support structure has a generally sinusoidal configuration with the peaks extending toward the first and second major surfaces; and wherein when the material body is elongated into the second position, the support structure is at least partially straightened so that the support structure is more linear, relative to when the material body is in the first position, the straightening of the support structure causing energy to be dissipated and generally preventing further elongation of the elastomer layer along the stretch axis past the second position.

* * * * *